(12) United States Patent
Morgan et al.

(10) Patent No.: US 7,176,222 B2
(45) Date of Patent: *Feb. 13, 2007

(54) SYNTHESES OF UREAS

(75) Inventors: Bradley Paul Morgan, Moraga, CA (US); George Petros Yiannikouros, Florence, SC (US); Michael P. Cruskie, Jr., Florence, SC (US); Christopher Roy Goss, Florence, SC (US)

(73) Assignee: Cytokinetics, Inc., South San Francisco, CA (US)

( * ) Notice: Subject to any disclaimer, the term of this patent is extended or adjusted under 35 U.S.C. 154(b) by 64 days.

This patent is subject to a terminal disclaimer.

(21) Appl. No.: 11/032,227

(22) Filed: Jan. 11, 2005

(65) Prior Publication Data

US 2006/0025470 A1 Feb. 2, 2006

Related U.S. Application Data

(60) Provisional application No. 60/616,341, filed on Oct. 5, 2004, provisional application No. 60/591,525, filed on Jul. 27, 2004, provisional application No. 60/591,338, filed on Jul. 27, 2004.

(51) Int. Cl.
| | |
|---|---|
| *A61K 31/45* | (2006.01) |
| *A61K 31/4439* | (2006.01) |
| *A61K 31/17* | (2006.01) |
| *C07C 273/18* | (2006.01) |
| *C07C 275/28* | (2006.01) |
| *C07D 211/98* | (2006.01) |
| *C07D 401/12* | (2006.01) |

(52) U.S. Cl. ............ 514/318; 514/343; 514/597; 546/194; 546/278.4; 564/50

(58) Field of Classification Search ........ 546/194, 546/278.4; 564/50
See application file for complete search history.

(56) References Cited

U.S. PATENT DOCUMENTS

| | | | |
|---|---|---|---|
| 3,907,782 | A | 9/1975 | Edwards |
| 3,939,169 | A | 2/1976 | Edwards |
| 5,162,360 | A | 11/1992 | Creswell et al. |
| 5,919,811 | A | 7/1999 | Conti et al. |
| 5,962,483 | A | 10/1999 | Warrellow et al. |
| 5,972,975 | A | 10/1999 | Esser et al. |
| 6,001,860 | A | 12/1999 | Hamanaka |
| 6,174,905 | B1 | 1/2001 | Suzuki et al. |
| 6,207,809 | B1 | 3/2001 | Nestler |
| 6,262,083 | B1 | 7/2001 | Moon et al. |
| 6,329,395 | B1 | 12/2001 | Dugar et al. |
| 6,573,264 | B1 | 6/2003 | Zablocki et al. |
| 6,645,990 | B2 | 11/2003 | Askew et al. |
| 6,656,971 | B2 | 12/2003 | Wu et al. |
| 6,670,376 | B1 | 12/2003 | Moran et al. |
| 6,696,576 | B2 | 2/2004 | Baumann et al. |
| 2003/0045552 | A1 | 3/2003 | Robarge et al. |
| 2003/0207872 | A1 | 11/2003 | Riedl et al. |
| 2005/0159416 | A1* | 7/2005 | Morgan et al. .......... 514/232.5 |

FOREIGN PATENT DOCUMENTS

| | | |
|---|---|---|
| JP | 11-302173 | 11/1999 |
| JP | 2000-256194 | 9/2000 |
| JP | 2002-220338 | 8/2002 |
| WO | WO 96/10559 A1 | 4/1996 |
| WO | WO 98/50346 A2 | 11/1998 |
| WO | WO 99/64394 A1 | 12/1999 |
| WO | WO 01/25190 A1 | 4/2001 |
| WO | WO 02/00626 A1 | 1/2002 |
| WO | WO 02/00632 A1 | 1/2002 |
| WO | WO 02/06246 A1 | 1/2002 |
| WO | WO 02/14311 A2 | 2/2002 |
| WO | WO 02/059106 A1 | 8/2002 |
| WO | WO 02/064576 A1 | 8/2002 |
| WO | WO 02/070462 A1 | 9/2002 |
| WO | WO 02/092576 A1 | 11/2002 |
| WO | WO 03/007942 A1 | 1/2003 |
| WO | WO 03/013523 A1 | 2/2003 |
| WO | WO 03/022820 A1 | 3/2003 |
| WO | WO 03/024933 A1 | 3/2003 |
| WO | WO 03/042164 A1 | 5/2003 |
| WO | WO 03/062224 A1 | 7/2003 |
| WO | WO 03/062235 A1 | 7/2003 |
| WO | WO 03/074501 A1 | 9/2003 |
| WO | WO 03/082278 A1 | 10/2003 |
| WO | WO 03/082808 A1 | 10/2003 |
| WO | WO 03/082861 A2 | 10/2003 |
| WO | WO 03/088967 A1 | 10/2003 |
| WO | WO 03/091229 A1 | 11/2003 |
| WO | WO 03/093250 A2 | 11/2003 |
| WO | WO 03/097576 A2 | 11/2003 |
| WO | WO 2004/000831 A1 | 12/2003 |
| WO | WO 2004/002481 A1 | 1/2004 |
| WO | WO 2004/013102 A1 | 2/2004 |
| WO | WO 2004/013132 A1 | 2/2004 |
| WO | WO 2004/019958 A1 | 3/2004 |
| WO | WO 2004/024729 A1 | 3/2004 |
| WO | WO 2004/039306 A2 | 5/2004 |

* cited by examiner

OTHER PUBLICATIONS

International Search Report and Written Opinion mailed Jan. 14, 2005, for Application No. PCT/US04/01069, filed Jan. 14, 2004.

*Primary Examiner*—Joseph K. McKane
*Assistant Examiner*—Jason M. Nolan
(74) *Attorney, Agent, or Firm*—Finnegan, Henderson, Farabow, Garrett & Dunner, L.L.P.

(57) ABSTRACT

The present invention provides intermediates, synthetic methods and novel urea compositions of matter.

51 Claims, No Drawings

SYNTHESES OF UREAS

This application claims the benefit of provisional U.S. Applications No. 60/616,341, filed Oct. 5, 2004; Ser. No. 60/591,338, filed Jul. 27, 2004; and Ser. No. 60/591,525, filed Jul. 27, 2004, and claims the benefit of co-pending application PCT/US04/01069, each incorporated herein by reference.

This invention relates to the synthesis of certain substituted urea derivatives, particularly to compounds that selectively modulate the cardiac sarcomere, and specifically to compounds, pharmaceutical compositions and methods of treatment for systolic heart failure, including congestive heart failure.

Inotropes are drugs that increase the contractile ability of the heart. As a group, all current inotropes have failed to meet the gold standard for heart failure therapy, i.e., to prolong patient survival. In addition, current agents are poorly selective for cardiac tissue, in part leading to recognized adverse effects that limit their use. Despite this fact, intravenous inotropes continue to be widely used in acute heart failure (e.g., to allow for reinstitution of oral medications or to bridge patients to heart transplantation) whereas in chronic heart failure, orally given digoxin is used as an inotrope to relieve patient symptoms, improve the quality of life, and reduce hospital admissions.

Given the limitations of current agents, new approaches are needed to improve cardiac function in congestive heart failure. The most recently approved short-term intravenous agent, milrinone, is now nearly fifteen years old. The oral drug, digoxin, is over 200 hundred years old. There remains a need for agents that exploit new mechanisms of action and may have better outcomes in terms of relief of symptoms, safety, and patient mortality, both short-term and long-term. New agents with an improved therapeutic index over current agents will provide a means to achieve these clinical outcomes.

PCT Publication No. WO 2004/064730 describes certain substituted urea derivatives, particularly compounds that selectively modulate the cardiac sarcomere, and specifically compounds, pharmaceutical compositions and methods of treatment for systolic heart failure, including congestive heart failure.

Development of ureas, and particularly, optically active ureas, for new therapeutic indications has increased the need for producing these enantiomerically pure active agents. While effective for producing research quantities, the prior synthetic approaches may be too lengthy and uneconomical for production of larger scale batches of compound. Intermediate chemical resolutions may require considerable time and result in relatively low yields. Moreover, certain reagents that are acceptable in small-scale syntheses are generally undesirable for large-scale production. Thus, there remains a need for improved urea syntheses, particularly for the larger scale production of enantiomerically pure urea.

In accordance with the objects outlined above, the present invention provides intermediates and synthetic methods for the preparation of substituted ureas. In some embodiments, the invention provides for methods for the synthesis of an enantiomerically pure urea comprising the use, as a starting material, of an enantiomerically pure compound of Formula 101:

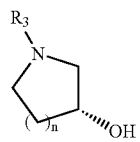

101 where:
$R_3$ is chosen from optionally substituted acyl, optionally substituted alkoxycarbonyl, amidino, and sulfonyl; and
n is 1 or 2.

In some embodiments, the method further comprises the steps of:
A) contacting a compound of Formula 101 with a base, and
B) reacting the product of step A) with a compound of Formula 102 to yield a compound of Formula 103:

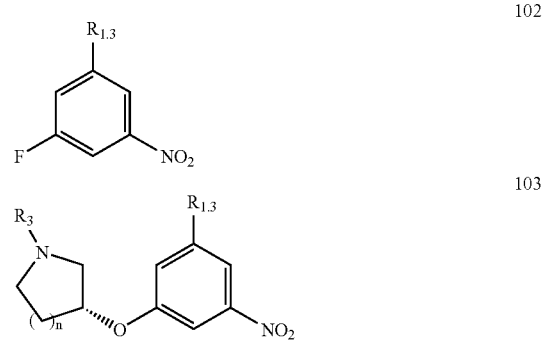

where
$R_{1.3}$ is chosen from hydrogen, halo, optionally substituted heteroaryl, and nitro.

In some embodiments, the method further comprises the step of:
C) converting a compound of Formula 103 to a compound of Formula 105:

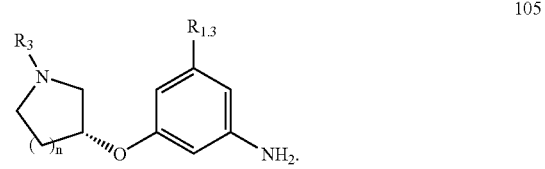

105

In some embodiments, the step of converting a compound of Formula 103 to a compound of Formula 105 comprises contacting a compound of Formula 103 with a catalyst and ammonium formate. In some embodiments, the step of converting a compound of Formula 103 to a compound of Formula 105 comprises contacting a compound of Formula 103 with a catalyst and hydrogen gas.

In some embodiments, the method further comprises the step of:
D) converting a compound of Formula 105 to a compound of Formula I:

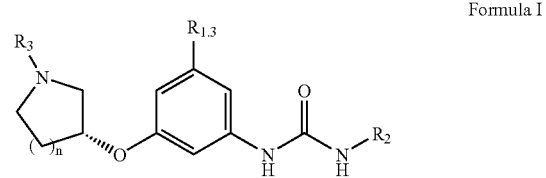

Formula I where:
$R_{1.3}$ is chosen from hydrogen, halo, optionally substituted heteroaryl, and nitro;

R$_2$ is chosen from optionally substituted aryl, optionally substituted aralkyl, optionally substituted cycloalkyl, optionally substituted heteroaryl, optionally substituted heteroaralkyl, and optionally substituted heterocyclyl, R$_3$ is chosen from optionally substituted acyl, optionally substituted alkoxycarbonyl, amidino, and sulfonyl; and n is 1 or 2.

In some embodiments, the step of converting a compound of Formula 105 to a compound of Formula I, comprises reacting a compound of Formula 105 with a compound of the formula R$_2$—NCO. In some embodiments, a compound of Formula 105 is converted to the corresponding acid addition salt prior to reaction with a compound of the formula R$_2$—NCO.

In some embodiments, the invention further provides a method for the synthesis of an enantiomerically pure compound of Formula I:

Formula I

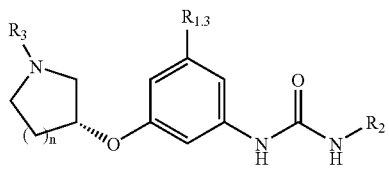

where:

R$_{1.3}$ is chosen from hydrogen, halo, optionally substituted heteroaryl, and nitro;

R$_2$ is chosen from optionally substituted aryl, optionally substituted aralkyl, optionally substituted cycloalkyl, optionally substituted heteroaryl, optionally substituted heteroaralkyl, and optionally substituted heterocyclyl;

R$_3$ is chosen from optionally substituted acyl, optionally substituted alkoxycarbonyl, amidino, and sulfonyl; and n is 1 or 2, wherein the method comprises at least one of the steps:

A) contacting a base with an enantiomerically pure compound of Formula 101:

101

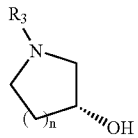

B) reacting the product of step A with a compound of Formula 102:

102

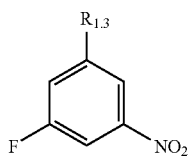

and

C) converting the product of step B to the compound of Formula I.

In some embodiments, the step of converting the product of step B to the compound of Formula I, comprises the steps of:

D) reducing the product of step B to the corresponding amine of Formula 105:

105

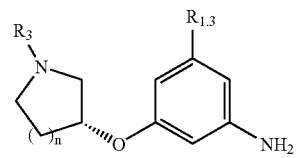

and

E) reacting the product of step D with a compound of the formula O=C=N—R$_2$ wherein R$_2$ is chosen from optionally substituted aryl, optionally substituted aralkyl, optionally substituted cycloalkyl, optionally substituted heteroaryl, optionally substituted heteroaralkyl, and optionally substituted heterocyclyl.

In some embodiments, the invention provides compositions of matter comprising an enantiomerically pure compound represented by Formula I:

Formula I

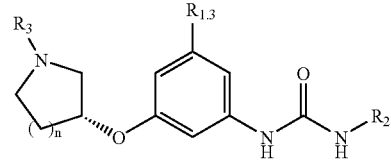

where:

R$_{1.3}$ is chosen from hydrogen, halo, optionally substituted heteroaryl, and nitro;

R$_2$ is chosen from optionally substituted aryl, optionally substituted aralkyl, optionally substituted cycloalkyl, optionally substituted heteroaryl, optionally substituted heteroaralkyl, and optionally substituted heterocyclyl;

R$_3$ is chosen from optionally substituted acyl, optionally substituted alkoxycarbonyl, amidino, and sulfonyl; and n is 1 or 2, or a pharmaceutically acceptable salt thereof, having a detectable amount of at least one of the following:

A) a compound of Formula 104:

104

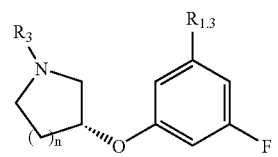

wherein n, R$_{1.3}$, and R$_3$ are as described herein;

B) a compound of Formula 114:

114

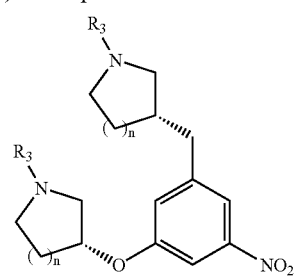

wherein n and R$_3$ are as described herein;

C) a compound of Formula 106:

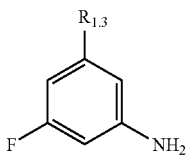

wherein R<sub>1.3</sub> is as described herein;

D) a compound of Formula 116:

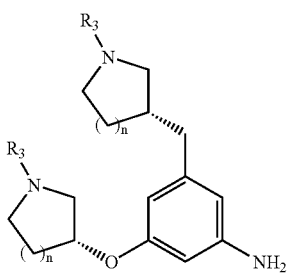

wherein n and R$_3$ are as described herein;

E) a compound of Formula 108:

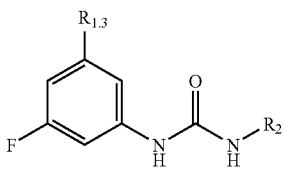

wherein R$_{1.3}$ and R$_2$ are as described herein;

F) a compound of Formula 118:

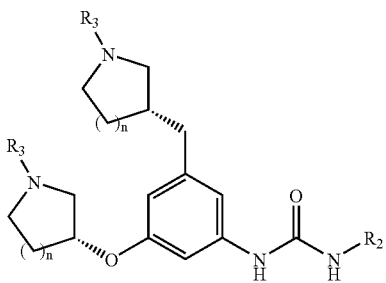

wherein n, R$_3$, and R$_2$ are as described herein;

G) a compound of Formula 120:

wherein R$_2$ is as described herein; and/or

H) a reagent employed in the synthesis of any of the foregoing.

In some embodiments, the invention provides for the use of an enantiomerically pure compound of Formula 101:

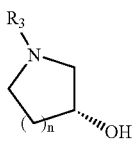

where:
R$_3$ is chosen from optionally substituted acyl, optionally substituted alkoxycarbonyl, amidino, and sulfonyl; and n is 1 or 2, as a starting material for the synthesis of an enantiomerically pure urea of Formula I:

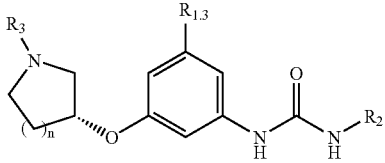

Formula I wherein:
R$_{1.3}$ is chosen from hydrogen, halo, optionally substituted heteroaryl, and nitro;
R$_2$ is chosen from optionally substituted aryl, optionally substituted aralkyl, optionally substituted cycloalkyl, optionally substituted heteroaryl, optionally substituted heteroaralkyl, and optionally substituted heterocyclyl;
R$_3$ is chosen from optionally substituted acyl, optionally substituted alkoxycarbonyl, amidino, and sulfonyl; and
n is 1 or 2, or a pharmaceutically acceptable salt thereof.

As used in the present specification, the following words and phrases are generally intended to have the meanings as set forth below, except to the extent that the context in which they are used indicates otherwise. The following abbreviations and terms have the indicated meanings throughout:

Ac=acetyl
Boc=t-butyloxy carbonyl
c-=cyclo
CBZ=carbobenzoxy=benzyloxycarbonyl
DCM=dichloromethane=methylene chloride=CH$_2$Cl$_2$
DIEA=N,N-diisopropylethylamine
DIPEA=N,N-diisopropylethylamine
DMF=N,N-dimethylformamide
DMSO=dimethyl sulfoxide
Et=ethyl
EtOAc=ethyl acetate
EtOH=ethanol
GC=gas chromatograghy
h=hour
Me=methyl
min=minute
mL=milliliter
MTBE=methyl tertiary butyl ether
NMP=N-methylpyrrolidone
Ph=phenyl
PMA=Phosphomolybdic Acid
PyBroP=bromo-tris-pyrrolidinophosphonium hexafluorophosphate
RBF=round bottom flask
rt=room temperature
s-=secondary
t-=tertiary
TFA=trifluoroacetic acid
THF=tetrahydrofuran
TLC=thin layer chromatography The term "optional" or "optionally" means that the subsequently described event or circumstance may or may not occur, and that the description includes instances where said event or circumstance occurs and instances in which it does not. For example, "optionally substituted alkyl" refers to either "alkyl" or "substituted alkyl," as defined below. It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups) that are sterically impractical, synthetically non-feasible and/or inherently unstable.

"Alkyl" is intended to include linear, branched, or cyclic hydrocarbon structures and combinations thereof. Lower alkyl refers to alkyl groups of from 1 to 5 carbon atoms. Examples of lower alkyl groups include methyl, ethyl, propyl, isopropyl, butyl, s- and t-butyl and the like. In some embodiments, alkyl groups are of from $C_{20}$ or below. In some embodiments, alkyl groups are of $C_{13}$ or below. In some embodiments, alkyl groups are of $C_6$ and below. Cycloalkyl is a subset of alkyl and includes cyclic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl and alkynyl groups; it is intended to include cyclohexylmethyl, vinyl, allyl, isoprenyl and the like. Alkylene is another subset of alkyl, referring to the same groups as alkyl, but having two points of attachment. Examples of alkylene include ethylene (—$CH_2CH_2$—), propylene (—$CH_2CH_2CH_2$—), dimethylpropylene (—$CH_2C(CH_3)_2CH_2$—) and cyclohexylpropylene (—$CH_2CH_2CH(C_6H_{13})$—). When an alkyl group having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

The term "alkoxy" or "alkoxyl" refers to the group —O-alkyl, such as including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to alkoxy groups containing one to four carbons.

The term "substituted alkoxy" refers to the group —O-(substituted alkyl). In some embodiments, a substituted alkoxy group is "polyalkoxy" or —O-(optionally substituted alkylene)-(optionally substituted alkoxy), and includes groups such as —$OCH_2CH_2OCH_3$, and glycol ethers such as polyethyleneglycol and —$O(CH_2CH_2O)_xCH_3$, where x is an integer of 2–20, such as 2–10, for example, 2–5. In some embodiments, a substituted alkoxy group is a hydroxyalkoxy such as —$OCH_2(CH_2)_yOH$, where y is an integer of 1–10, such as 1–4.

By "alkoxycarbonyl" is meant an ester group of the formula (alkoxy)(C=O)— attached through the carbonyl carbon wherein the alkoxy group has the indicated number of carbon atoms. Thus, a $C_1$–$C_6$ alkoxycarbonyl group is an alkoxy group having from 1 to 6 carbon atoms attached through its oxygen to a carbonyl linker.

"Acyl" refers to groups of from 1 to 10 carbon atoms of a straight, branched, cyclic configuration, saturated, unsaturated and aromatic and combinations thereof, attached to the parent structure through a carbonyl functionality. One or more carbons in the acyl group may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. "Lower-acyl" refers to groups containing one to four carbons and "acyloxy" refers to the group O-acyl.

The term "amino" refers to the group —$NH_2$. The term "substituted amino" refers to the group —NHR or —NRR where each R is independently selected from the group: optionally substituted alkyl, optionally substituted alkoxy, optionally substituted amino, optionally substituted aryl, optionally substituted heteroaryl, optionally substituted heterocyclyl, acyl, alkoxycarbonyl, sulfanyl, sulfinyl and sulfonyl, e.g., diethylamino, methylsulfonylamino, furanyloxy-sulfonamino.

The term "amidino" refers to the group —C(=NR)—$NR_2$ where each R is independently selected from the group: optionally substituted alkyl, optionally substituted aryl, optionally substituted heteroaryl, optionally substituted heterocyclyl, acyl, alkoxycarbonyl, sulfanyl, sulfinyl and sulfonyl.

"Aryl" encompasses:
  5- and 6-membered carbocyclic aromatic rings, for example, benzene;
  bicyclic ring systems wherein at least one ring is carbocyclic and aromatic, for example, naphthalene, indane, and tetralin; and
  tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined below.

"Aralkoxy" refers to the group —O-aralkyl. Similarly, "heteroaralkoxy" refers to the group —O-heteroaralkyl; "aryloxy" refers to —O-aryl; and "heteroaryloxy" refers to the group —O-heteroaryl.

"Aralkyl" refers to a group in which an aryl moiety is attached to the parent structure via an alkyl group. Examples include benzyl, phenethyl, phenylvinyl, phenylallyl and the like. "Heteroaralkyl" refers to a group in which a heteroaryl moiety is attached to the parent structure via an alkyl group. Examples include furanylmethyl, pyridinylmethyl, pyrimidinylethyl and the like.

"ATPase" refers to an enzyme that hydrolyzes ATP. ATPases include proteins comprising molecular motors such as the myosins.

The term "substantially optically pure" or "enantiomerically pure" means having at least about 95% of the described enantiomer with no single impurity greater than about 1% and preferably, at least about 97.5% enantiomeric excess.

"Halogen" or "halo" refers to fluorine, chlorine, bromine or iodine. Fluorine, chlorine and bromine are preferred. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Heteroaryl" encompasses:
  5- to 7-membered aromatic, monocyclic rings containing one or more, for example, from 1 to 4, or in certain embodiments, from 1 to 3, heteroatoms chosen from N, O, and S, with the remaining ring atoms being carbon; and bicyclic heterocyclic rings containing one or more, for example, from 1 to 4, or in certain embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, systems (as numbered from the linkage position assigned priority 1), such as 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

"Heterocycle" or "heterocyclyl" refers to a cycloalkyl group in which one to four of the carbons is replaced by a heteroatom such as oxygen, nitrogen or sulfur. a 4-, 5-, 6- or 7-membered non-aromatic ring containing 1–4 heteroatoms, a bicyclic 8-, 9- or 10-membered non-aromatic ring system containing 1–4 (or more) heteroatoms, or a tricyclic 11- to 14-membered non-aromatic ring system containing 1–4 (or more) heteroatoms; the heteroatoms are selected from O, N or S. Examples include pyrrolidine, tetrahydrofuran, tetrahydro-thiophene, thiazolidine, piperidine, tetrahydro-pyran, tetrahydro-thiopyran, piperazine, morpholine, thiomorpholine and dioxane. Heterocyclyl also includes ring systems including unsaturated bonds, provided the number and placement of unsaturation does not render the group aromatic. Examples include imidazoline, oxazoline, tetrahydroisoquinoline, benzodioxan, benzodioxole and 3,5-dihydrobenzoxazinyl. Examples of substituted heterocyclyl include 4-methyl-1-piperazinyl and 4-benzyl-1-piperidinyl.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)— and (S)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts that retain the biological effectiveness and properties of the compounds of this invention and, which are not biologically or otherwise undesirable. In many cases, the compounds of this invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. In some embodiments, the salt is an ammonium, potassium, sodium, calcium, or magnesium salt. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

The term "solvate" refers to a compound (e.g., a compound of Formula I or a pharmaceutically acceptable salt thereof) in physical association with one or more molecules of a pharmaceutically acceptable solvent. It will be understood that phrases such as "a compound of Formula I or a pharmaceutically acceptable salt or solvate thereof" are intended to encompass the compound of Formula I, a pharmaceutically acceptable salt of the compound, a solvate of the compound, and a solvate of a pharmaceutically acceptable salt of the compound.

The terms "solvent", "inert organic solvent" or "inert solvent" mean a solvent inert under the conditions of the reaction being described in conjunction therewith. Solvents employed in synthesis of the compounds of the invention include, for example, methanol, acetone, water, acetonitrile, 1,4-dioxane, dimethylformamide, benzene, toluene, tetrahydrofuran, chloroform, methylene chloride (or dichloromethane), diethyl ether, pyridine and the like, as well as mixtures thereof. Unless specified to the contrary, the solvents used in the reactions of the present invention are inert organic solvents.

"Substituted-" alkyl, aryl, heteroaryl and heterocyclyl refer respectively to alkyl, aryl, heteroaryl and heterocyclyl wherein one or more (up to 5, such as up to 3) hydrogen atoms are replaced by a substituent independently chosen from:

—$R^a$, —$OR^b$, —$O(C_1$-$C_2$ alkyl)O— (e.g., methylenedioxy-), —$SR^b$, guanidine, guanidine wherein one or more of the guanidine hydrogens are replaced with a group chosen from a lower-alkyl group, —$NR^bR^c$, halo, cyano, nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$CO_2R^b$, —$CONR^b R^c$, —$NR^cCOR^b$, —$SOR^a$, —$SO_2R^a$, —$SO_2NR^bR^c$, and —$NR^cSO_2R^a$, where $R^a$ is chosen from optionally substituted $C_1$–$C_6$ alkyl, optionally substituted aryl, and optionally substituted heteroaryl;

$R^b$ is chosen from H, optionally substituted $C_1$–$C_6$ alkyl, optionally substituted aryl, and optionally substituted heteroaryl; and $R^c$ is chosen from hydrogen and optionally substituted $C_1$–$C_4$ alkyl; where each optionally substituted group is unsubstituted or independently substituted with one or more, such as one, two, or three, substituents independently selected from $C_1$–$C_4$ alkyl, aryl, heteroaryl, aryl-$C_1$–$C_4$ alkyl-, heteroaryl-$C_1$–$C_4$ alkyl-, $C_1$–$C_4$ haloalkyl —$OC_1$–$C_4$ alkyl, —$OC_1$–$C_4$ alkylphenyl, —$C_1$–$C_4$ alkyl-OH, —$OC_1$–$C_4$ haloalkyl, halo, —OH, —$NH_2$, —$C_1$–$C_4$ alkyl-$NH_2$, —$N(C_1$–$C_4$ alkyl)($C_1$–$C_4$ alkyl), —$NH(C_1$–$C_4$ alkyl), —$N(C_1$–$C_4$ alkyl)($C_1$–$C_4$ alkylphenyl), —$NH(C_1$–$C_4$ alkylphenyl), cyano, nitro, oxo (as a substituent for heteroaryl), —$CO_2H$, —$C(O)OC_1$–$C_4$ alkyl, —$CON(C_1$–$C_4$ alkyl)($C_1$–$C_4$ alkyl), —$CONH(C_1$–$C_4$ alkyl), —$CONH_2$, —$NHC(O)(C_1$–$C_4$ alkyl), —$NHC(O)(phenyl)$, —$N(C_1$–$C_4$ alkyl)C(O)(C_1$–$C_4$ alkyl), —$N(C_1$–$C_4$ alkyl)C(O)(phenyl), —$C(O)C_1$–$C_4$ alkyl, —$C(O)C_1$–$C_4$ phenyl, —$C(O)C_1$–$C_4$ haloalkyl, —$OC(O)C_1$–$C_4$ alkyl, —$SO_2(C_1$–$C_4$ alkyl),—$SO_2$(phenyl), —$SO_2(C_1$–$C_4$ haloalkyl), —$SO_2NH_2$,—$SO_2NH(C_1$–$C_4$ alkyl), —$SO_2NH(phenyl)$, —$NHSO_2(C_1$–$C_4$ alkyl), —$NHSO_2(phenyl)$, and —$NHSO_2(C_1$–$C_4$ haloalkyl).

The term "sulfanyl" includes the groups: —S-(optionally substituted alkyl), —S-(optionally substituted aryl), —S-(optionally substituted heteroaryl), and —S-(optionally substituted heterocycloalkyl). Hence, sulfanyl includes the group $C_1$–$C_6$ alkylsulfanyl.

The term "sulfinyl" includes the groups: —S(O)—H, —S(O)-(optionally substituted alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups: —S($O_2$)—H, —S($O_2$)-(optionally substituted alkyl), —S($O_2$)-optionally substituted aryl), —S($O_2$)-optionally substituted heteroaryl), —S($O_2$)-(optionally substituted heterocycloalkyl), —S($O_2$)-(optionally substituted alkoxy), —S($O_2$)-optionally substituted aryloxy), —S($O_2$)-optionally substituted heteroaryloxy), —S($O_2$)-(optionally substituted heterocyclyloxy); and —S($O_2$)-(optionally substituted amino).

The term "therapeutically effective amount" or "effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the particular compound of Formula I chosen, the dosing regimen to be followed, timing of administration, the manner of administration and the like, all of which can readily be determined by one of ordinary skill in the art.

By a "detectable amount" of a compound is meant a sufficient amount to give positive identification but not necessarily quantitation of the compound by any suitable analytical technique, for example HPLC.

The terms "reacting" and "contacting" are intended to represent bringing the chemical reactants together under conditions such to cause the chemical reaction indicated to take place.

The term "treatment" or "treating" refers to any treatment of a disease in a mammal, including:
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

The present invention provides intermediates and synthetic methods for the synthesis of enantiomerically pure ureas. In some embodiments, the invention provides methods for the synthesis of an enantiomerically pure urea comprising the use, as a starting material, of an enantiomerically pure compound of Formula 101:

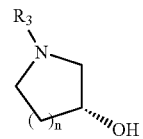

101 where:
$R_3$ is chosen from optionally substituted acyl, optionally substituted alkoxycarbonyl, amidino, and sulfonyl; and
n is 1 or 2.

In some embodiment, the method further comprises the steps of:
A) contacting a compound of Formula 101 with a base, and
B) reacting the product of step A) with a compound of Formula 102 to yield a compound of Formula 103:

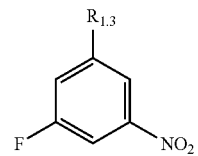

102

-continued

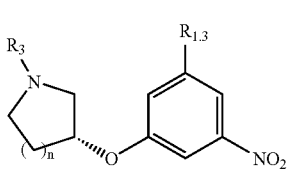
103 where
R$_{1.3}$ is chosen from hydrogen, halo, optionally substituted heteroaryl, optionally substituted alkyl and nitro;
R$_3$ is chosen from optionally substituted acyl, optionally substituted alkoxycarbonyl, amidino, and sulfonyl; and
n is 1 or 2.

In some embodiments, the method further comprises the steps of:
C) converting a compound of Formula 103 to a compound of Formula 105:

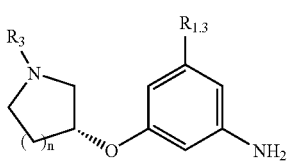
105 where
R$_{1.3}$ is chosen from hydrogen, halo, optionally substituted heteroaryl, optionally substituted alkyl, and nitro; R$_3$ is chosen from optionally substituted acyl, optionally substituted alkoxycarbonyl, amidino, and sulfonyl; and
n is 1 or 2.

In some embodiments, converting a compound of Formula 103 to a compound of Formula 105 comprises contacting a compound of Formula 103 with a catalyst and ammonium formate. In some embodiments, the step of converting a compound of Formula 103 to a compound of Formula 105 comprises contacting a compound of Formula 103 with a catalyst and hydrogen gas.

In some embodiments, the method further comprises the step of:
D converting a compound of Formula 105 to a compound of Formula I:

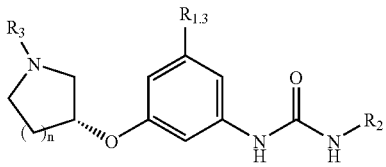
Formula I where:
R$_{1.3}$ is chosen from hydrogen, halo, optionally substituted heteroaryl, optionally substituted alkyl, and nitro;
R$_2$ is chosen from optionally substituted aryl, optionally substituted aralkyl, optionally substituted cycloalkyl, optionally substituted heteroaryl, optionally substituted heteroaralkyl, and optionally substituted heterocyclyl;
R$_3$ is chosen from optionally substituted acyl, optionally substituted alkoxycarbonyl, amidino, and sulfonyl; and
n is 1 or 2.

In some embodiments, converting a compound of Formula 105 to a compound of Formula I, comprises reacting a compound of Formula 105 with a compound of the formula R$_2$—NCO. In some embodiments, the compound of Formula 105 is converted to the corresponding acid addition salt prior to reaction with a compound of the formula R$_2$—NCO.

In some embodiments, the invention provides for the synthesis of an enantiomerically pure compound of Formula I:

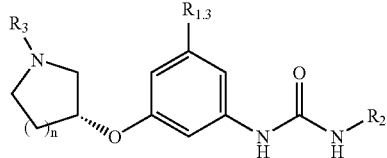
Formula I where:
R$_{1.3}$ is chosen from hydrogen, halo, optionally substituted heteroaryl, optionally substituted alkyl, and nitro;
R$_2$ is chosen from optionally substituted aryl, optionally substituted aralkyl, optionally substituted cycloalkyl, optionally substituted heteroaryl, optionally substituted heteroaralkyl, and optionally substituted heterocyclyl,
R$_3$ is chosen from optionally substituted acyl, optionally substituted alkoxycarbonyl, amidino, and sulfonyl; and
n is 1 or 2, via a method including at least one of the steps:
A) contacting a base with an enantiomerically pure compound of Formula 101:

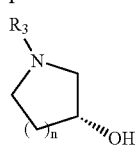
101

B) reacting the product of step A with a compound of Formula 102:

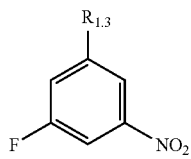
102 and
C) converting the product of step B to the compound of Formula I. In some embodiments, converting the product of step B to the compound of Formula I, comprises the steps of:
D) reducing the product of step B to the corresponding amine of Formula 105:

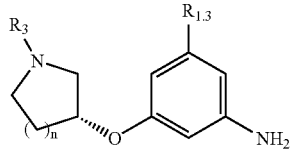
105 and
E) reacting the product of step D with a compound of the formula O=C=N—R$_2$ wherein R$_2$ is chosen from optionally substituted aryl, optionally substituted aralkyl, optionally substituted cycloalkyl, optionally substituted heteroaryl, optionally substituted heteroaralkyl, and optionally substituted heterocyclyl.

The compounds of formula 101 and 102, and other reactants, are commercially available, e.g., from Aldrich Chemical Company, Milwaukee, Wis., or can be readily prepared by those skilled in the art using commonly employed methodology.

Unless specified to the contrary, the reactions described herein take place at atmospheric pressure, generally within a temperature range from −10° C. to 150° C. Further, unless otherwise specified, the reaction times and conditions are intended to be approximate, e.g., taking place at about atmospheric pressure within a temperature range of about −10C. to about 150° C. over a period of about 1 to about 24 hours.

The isolation and purification procedures described herein can be effected, if desired, by any suitable separation or purification procedure such as, for example, filtration, extraction, crystallization, column chromatography, thin-layer chromatography or preparative chromatography, or a combination of these procedures. Specific illustrations of suitable separation and isolation procedures can be had by reference to the examples hereinbelow. However, other equivalent separation or isolation procedures can, of course, also be used.

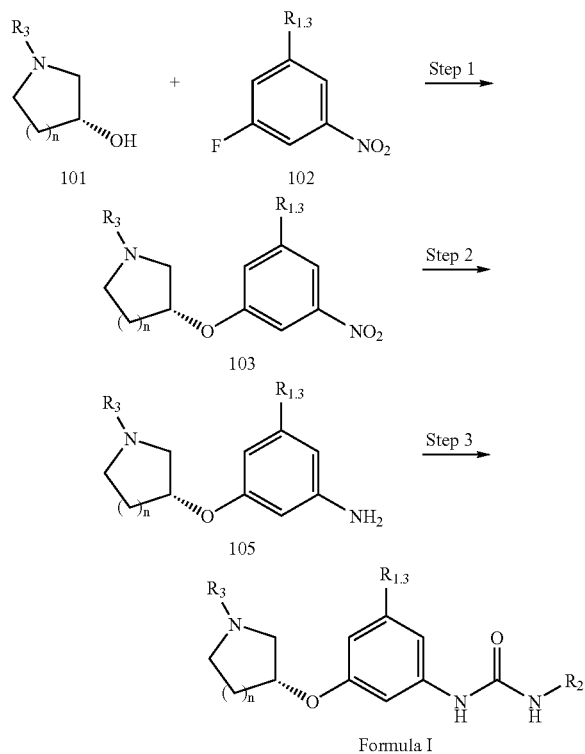

Reaction Scheme 1

Referring to Reaction Scheme 1, Step 1, a solution of a compound of Formula 101 in an inert solvent such as NMP is slowly added (over a period of about 60 to 120 minutes) to a cooled solution of an excess, such as about 1.1 equivalents or more (such as about 1.3 to about 1.5 equivalents) of a base (such as sodium hydride, for example, 60% dispersion of sodium hydride in mineral oil) in an inert solvent such as NMP. Alternatively, the base is added portionwise to the solution of a compound of Formula 101 in an inert solvent such as NMP. In certain embodiments, the solution is cooled to less than about 10° C., such as about 0° C., and is then stirred for several hours (such as about 2 hours).

The solution is added slowly (over a period of about 2 hours) to a cooled (such as 0° C.) solution of about an equivalent (such as about 0.95 to about 1.05 equivalents) of a compound of Formula 102 in an inert solvent such as NMP. Alternatively, the compound of Formula 102, optionally in an inert solvent, is added slowly to the solution of a compound of Formula 101. The mixture is maintained at about 0° C. to about 15° C. during the addition and is then warmed to about 70° C. The mixture is maintained at about 70° C. for several hours (such as 10 or more, such as 11, hours). The product, a compound of Formula 103, is isolated and optionally purified.

In some embodiments, the compound of Formula 103 is present as part of a mixture. For example, in some embodiments, the mixture comprises a compound of Formula 103 and a compound of Formula 104:

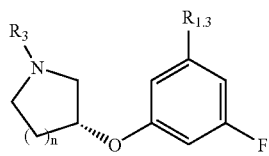

104 wherein n, $R_{1.3}$, and $R_3$ are as described herein. In some embodiments, the mixture comprises a compound of Formula 103 and a compound of Formula 114:

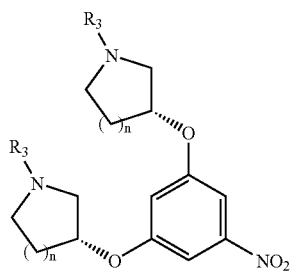

114 wherein n and $R_3$ are as described herein. In some embodiments, the mixture comprises a compound of Formula 103 and a compound of Formula 102. In some embodiments, the mixture comprises a compound of Formula 103, a compound of Formula 104, and a compound of Formula 114. In some embodiments, the mixture comprises a compound of Formula 103, a compound of Formula 104, a compound of Formula 114, and a compound of Formula 102.

In some embodiments, the mixture is from about 80% to about 85% of a compound of Formula 103 and about 5% to about 10% of a compound of Formula 104.

In some embodiments, the compound of Formula 103 is enantiomerically pure. In some embodiments, the compound of Formula 103 has an enantiomeric excess of about 95% or more. In some embodiments, the compound of Formula 103 has an enantiomeric excess of about 98% or more. In some embodiments, the compound of Formula 103 has an enantiomeric excess of about 98%.

Referring to Reaction Scheme 1, Step 2, a compound of Formula 103 is converted to the corresponding amine of Formula 105. A solution of a compound of Formula 103 in a polar, protic solvent such as a lower alkanol, for example, methanol, is added to a solution of a catalyst (such as Pd/C, for example, 10% Pd/C or 20% PdOH/C, such as about 10% by weight of 10% Pd/C or about 5–6% by weight of 20% PdOH/C) in an inert solvent such as THF or a lower alkanol, for example, methanol.

In some embodiments, the solution is warmed, for example, to about 60-65° C. In some embodiments, a solution of an excess, such as two or more equivalents, for example, five equivalents, of ammonium formate in a polar, protic solvent such as water, is slowly added (over a period of 8 or more hours, such as 10 hours).

Alternatively, in some embodiments, hydrogen gas (at about 60 psi or more) is used to effect the reduction. The reaction is cooled to maintain an internal reaction temperature of less than about 60° C. for an initial time period and then cooled slowly to room temperature.

The product, a compound of Formula 105, is isolated and optionally purified, for example, using a Biotage Flash 150 column.

In some embodiments, the compound of Formula 103 is present as part of a mixture. For example, in some embodiments, the mixture comprises a compound of Formula 105 and a compound of Formula 106:

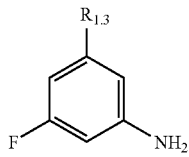

106 wherein $R_{1.3}$ is as described herein. In some embodiments, the mixture comprises a compound of Formula 105 and a compound of Formula 116:

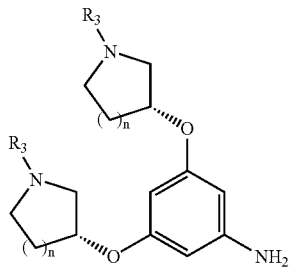

116 wherein n, and $R_3$ are as described herein.

In some embodiments, the compound of Formula 105 is enantiomerically pure. In some embodiments, the compound of Formula 105 has an enantiomeric excess of about 95% or more. In some embodiments, the compound of Formula 105 has an enantiomeric excess of about 98% or more. In some embodiments, the compound of Formula 105 has an enantiomeric excess of about 99%.

In some embodiments, the amine of Formula 105 is converted to the corresponding acid additional salt, such as the HCl salt. A solution of a compound of Formula 105 in an inert solvent such as ethyl acetate is cooled to about 0° C. To this solution is slowly added (over a period of about 10 or more minutes, such as about 20 minutes), a solution of HCl in an inert solvent (such as ether, for example, a 2 M solution of HCl in ether) while maintaining the reaction temperature below about 10° C. The solution is stirred at about 0° C. for several hours, such as about 2 hours). The product, the HCl salt of a compound of Formula 105, is isolated and optionally purified.

In some embodiments, the acid addition salt of a compound of Formula 105 is enantiomerically pure. In some embodiments, the acid additional salt of a compound of Formula 105 has an enantiomeric excess of about 95% or more. In some embodiments, the acid additional salt of a compound of Formula 105 has an enantiomeric excess of about 98% or more. In some embodiments, the acid additional salt of a compound of Formula 105 has an enantiomeric excess of about 99% or more.

Referring to Reaction Scheme 1, Step 3, about an equivalent or a slight excess, such as about 0.9 to about 1.1 equivalents) of a base such as DIPEA is added to a solution of a compound of Formula 105, or an acid addition salt of a compound of Formula 105, in an inert solvent such as dichloromethane or THF. The solution is cooled to about 0–10° C. An excess, such as 1.1 equivalents or more, of a compound of the formula O=C=N—$R_2$ is added. The mixture is warmed to room temperature and stirred for several hours. Additional aliquots of a compound of the formula O=C=N—$R_2$ may be added, if necessary. The product, a compound of Formula I, is isolated and optionally purified, for example by trituration in ethyl acetate or recrystallization.

In some embodiments, the compound of Formula I is present as part of a mixture. For example, in some embodiments, the mixture comprises a compound of Formula I and a compound of Formula 108:

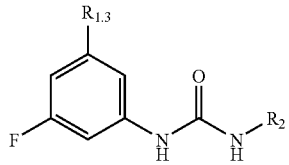

108 wherein $R_{1.3}$, and $R_2$ are as described herein. In some embodiments, the mixture comprises a compound of Formula I and a compound of Formula 118:

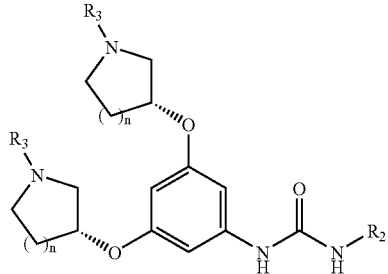

118 wherein n, $R_3$, and $R_2$ are as described herein.

In some embodiments, the mixture comprises a compound of Formula I and a compound of Formula 120:

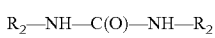

120 wherein $R_2$ is as described herein.

In some embodiments, a compound of Formula I is enantiomerically pure. In some embodiments, the compound of Formula I has an enantiomeric excess of about 95% or more. In some embodiments, the compound of Formula I has an enantiomeric excess of about 98% or more. In some embodiments, the compound of Formula I has an enantiomeric excess of about 99% or more. In some embodiments, the compound of Formula I has an enantiomeric excess of about 99%.

Reaction Scheme 2

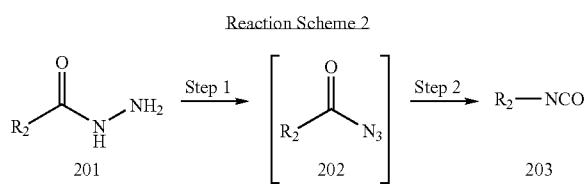

Referring to Reaction Scheme 2, Step 1, a compound of Formula 201 is contacted with an acid (such as aqueous hydrochloric acid, for example, 3 M HCl) at about 0° C. To this is added slowly (for example, over about 3 hours) a solution of an excess (such as about two equivalents) of sodium nitrite in a polar, protic solvent such as water while maintaining the internal temperature at about 0° C. Upon completion, the reaction mixture is neutralized (for example, by treatment with sodium bicarbonate). The aqueous solution is extracted with one or more nonpolar, aprotic solvents (for example, toluene and methyl t-butyl ether). The compound of Formula 202 is maintained as a solution for use in Step 2.

Referring to Reaction Scheme 2, Step 2, a solution of a compound of Formula 202 in a nonpolar, aprotic solvent such as toluene is heated from about 100° C. to about 110° C. The product, a compound of Formula 203, is isolated and purified.

Reaction Scheme 3

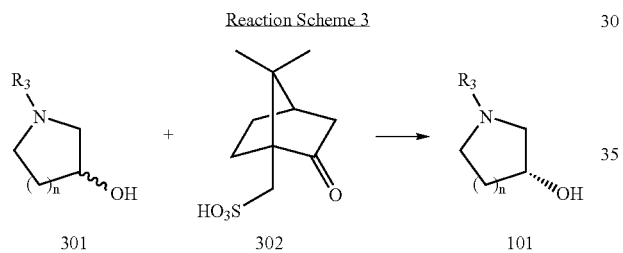

Referring to Reaction Scheme 3, a compound of Formula 301 is resolved into enantiomers via crystallization of diastereoisomeric salts with (1S)-(+)-10-camphorsulfonic acid. In some embodiments, a compound of Formula 301 wherein $R_3$ is hydrogen is treated with a chiral auxiliary, such as a compound of Formula 302, in a polar, protic solvent such as ethanol. The resulting diasteriomeric mixture of salts is then separated and the chiral auxiliary is removed to yield the compound of Formula 101. In some embodiments, the diasteromeric mixture is isolated and then treated with aqueous base (such as aqueous sodium bicarbonate) in a solution of a nonpolar, aprotic solvent such as dichloromethane and an acyl anhydride (such as acetic anhydride). The acylated diastereomieric mixture is separated and the chiral auxillary is removed to yield the product, a compound of Formula 101 wherein $R_3$ is acyl. See, for example, Hammer, C. F.; Weber, J. P. *Tetrahedron*, 1981, 37, 2172–2180.

Compounds prepared by the methods described herein and products incorporating them (e.g., pharmaceutical compositions) can be identified by the presence of a detectable amount of certain novel starting materials and/or reactants, such as a starting material (e.g., a compound of Formula 101 or 102) or a reactant (e.g., imidazole, sodium hydride, Pd/C or PdOH/C). While it is well known that pharmaceuticals must meet pharmacopoeia standards before approval and/or marketing, and that synthetic reagents or side products should not exceed the limits prescribed by pharmacopoeia standards, final compounds prepared by a process of the present invention may have minor, but detectable, amounts of such materials present, for example at levels in the range of 95% purity with no single impurity greater than 1%. These levels can be detected, e.g., by emission spectroscopy. It is important to monitor the purity of pharmaceutical compounds for the presence of such materials, which presence is additionally disclosed as a method of detecting use of a process of the invention.

The present invention provides a novel composition of matter or pharmaceutical composition comprising a compound or pharmaceutically acceptable salt of Formula I and a detectable amount of at least one of the following:

A) a compound of Formula 104:

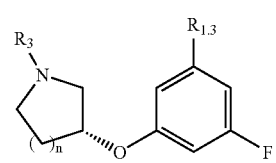

wherein n, $R_{1.3}$, and $R_3$ are as described herein;

B) a compound of Formula 114:

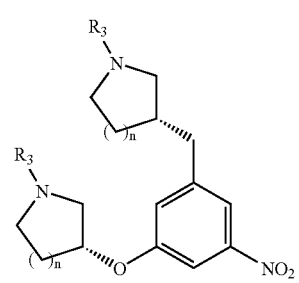

wherein n, and $R_3$ are as described herein;

C) a compound of Formula 106:

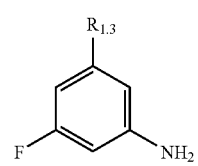

wherein $R_{1.3}$ are as described herein;

D) a compound of Formula 116:

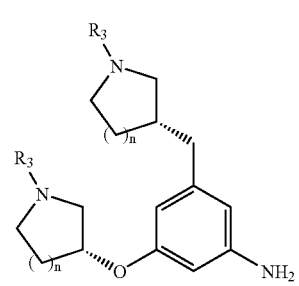

wherein n and $R_3$, are as described herein;

E) a compound of Formula 108:

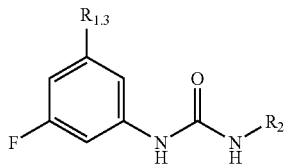

wherein $R_{1.3}$, and $R_2$ are as described herein;

F) a compound of Formula 118:

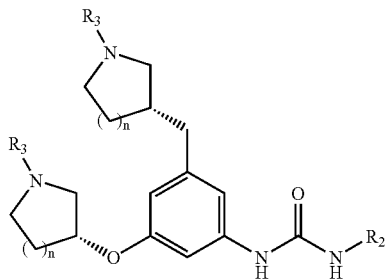

wherein n, $R_3$, and $R_2$ are as described herein;

G) a compound of Formula 120:

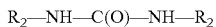

wherein $R_2$ is as described herein; and/or

H) a reagent (such as sodium hydride, or $Na_2CO_3$) employed in the synthesis of any of the foregoing.

In certain embodiments, $R_{1.3}$ is chosen from hydrogen, halo, optionally substituted heteroaryl, optionally substituted alkyl, and nitro. In certain embodiments, $R_{1.3}$ is optionally substituted heteroaryl (in some embodiments, pyridinyl or imidazolyl), nitro or halo. In certain embodiments, $R_{1.3}$ is optionally substituted pyridinyl, optionally substituted imidazolyl, nitro, or halo. In certain embodiments, $R_{1.3}$ is pyridinyl or fluoro. In certain embodiments, $R_{1.3}$ is fluoro.

In certain embodiments, $R_2$ is chosen from optionally substituted aryl, optionally substituted aralkyl, optionally substituted cycloalkyl, optionally substituted heteroaryl, optionally substituted heteroaralkyl, and optionally substituted heterocyclyl. In certain embodiments, $R_2$ is optionally substituted pyridinyl, optionally substituted pyrimidinyl, or optionally substituted pyridazinyl. In certain embodiments, the $R_2$ aryl or heteroaryl ring is substituted with one, two, or three of the following groups: optionally substituted lower alkyl, halo, hydroxy, cyano, substituted amino, nitro, methylenedioxy, ethelenedioxoy, optionally substituted heterocyclyl, sulfanyl, sulfonyl, —OR, —COR', —(CO)OR' and/or —(CO)N R'R' where each R' is independently hydrogen or optionally substituted lower alkyl (in some embodiments, R' being methyl in the cases of —OR' and —COR'). In certain embodiments, optionally substituted lower alkyl is methyl, hydroxymethyl, methoxymethyl, trifluoromethyl, ethyl, (amino)carbonylmethyl, (methylamino)carbonylmethyl, acetylaminomethyl, or hydroxyethyl. In certain embodiments, optionally substituted heterocyclyl is optionally substituted mopholinyl. In certain embodiments, sulfanyl is methylsulfanyl.

In certain embodiments, $R_2$ is optionally substituted phenyl, optionally substituted naphthyl, optionally substituted pyrrolyl, optionally substituted, thiazolyl, optionally substituted isooxazolyl, optionally substituted pyrazolyl, optionally substituted pyridinyl, optionally substituted pyrazinyl, optionally substituted pyrimidinyl, or optionally substituted pyridazinyl. In certain embodiments, $R_2$ has one or two optional substituents selected from: acetyl, lower alkyl, lower alkoxy, lower alkoxyalkyl, lower alkoxy carbonyl, hydroxy substituted lower alkyl, alkoxy substituted lower alkyl, carboxy, halo, and trifluoromethyl. In certain embodiments, $R_2$ is isooxazol-3-yl, 5-methyl-isooxazol-3-yl, isooxazol-5-yl, pyrazol-3-yl, pyrazinyl, substituted phenyl or optionally substuted pyridinyl. In certain embodiments, $R_2$ is phenyl having one or two substituents selected from: lower alkyl, lower alkoxy, halo, hydroxy and hydroxy substituted lower alkyl. In certain embodiments, $R_2$ is pyridin-2-yl, pyridin-3-yl or pyridin-4-yl optionally having one or more (such as one, two, or three, for example, one) substituent selected from: acetyl, lower alkyl, lower alkoxy, lower alkoxyalkyl, lower alkoxy carbonyl, carboxy and trifluoromethyl. In certain embodiments, $R_2$ is optionally-p-substituted pyridin-3-yl. In certain embodiments, $R_2$ is pyridin-3-yl optionally p-substituted with a member of the group: acetyl, methyl, ethyl, methoxy, methoxymethyl, hydroxy, hydroxymethyl and hydroxyethyl. In certain embodiments, $R_2$ is pyridin-3-yl or 6-methyl-pyridin-3-yl.

In certain embodiments, $R_3$ is chosen from optionally substituted acyl, optionally substituted alkoxycarbonyl, amidino, and sulfonyl. In certain embodiments, $R_3$ is chosen from acetyl, methoxyacetyl-, azetidine-1-carbonyl-, methoxycarbonyl-, ethoxycarbonyl-, dimethylaminocarbonyl-, methanesulfonyl-, ethane-2-sulfonyl-, propane-2-sulfonyl-, azetidin-1-yl-sulfonyl-, dimethylaminosulfonyl-, $N^1$-azetidin-1-yl-$N^2$-cyano-amidino-, and $N^2$-cyano-$N^1$,$N^1$-dimethyamidino-. In certain embodiments, $R_3$ is acetyl or dimethylaminosulfonyl-.

In certain embodiments, n is 1 or 2. In certain embodiments, n is 1. In certain embodiments, n is 2.

In certain embodiments, $R_{1.3}$ is optionally substituted pyridinyl, optionally substituted imidazolyl, nitro, or halo;

n is 1; and $R_3$ is chosen from optionally substituted acyl, optionally substituted alkoxycarbonyl, amidino, and sulfonyl (such as acetyl, methoxyacetyl-, azetidine-1-carbonyl-, methoxycarbonyl-, ethoxycarbonyl-, dimethylaminocarbonyl-, methanesulfonyl-, ethane-2-sulfonyl-, propane-2-sulfonyl-, azetidin-1-yl-sulfonyl-, dimethylaminosulfonyl-, $N^1$-azetidin-1-yl-$N^2$-cyano-amidino-, and $N^2$-cyano-$N^1$,$N^1$-dimethyamidino-).

In certain embodiments, $R_{1.3}$ is pyridinyl or fluoro;

n is 1; and $R_3$ is chosen from optionally substituted acyl, optionally substituted alkoxycarbonyl, amidino, and sulfonyl (such as acetyl, methoxyacetyl-, azetidine-1-carbonyl-, methoxycarbonyl-, ethoxycarbonyl-, dimethylaminocarbonyl-, methanesulfonyl-, ethane-2-sulfonyl-, propane-2-sulfonyl-, azetidin-1-yl-sulfonyl-, dimethylaminosulfonyl-, $N^1$-azetidin-1-yl-$N^2$-cyano-amidino-, and $N^2$-cyano-$N^1$,$N^1$-dimethyamidino-).

In certain embodiments, $R_{1.3}$ is fluoro;

n is 1; and $R_3$ is chosen from optionally substituted acyl, optionally substituted alkoxycarbonyl, amidino, and sulfonyl (such as acetyl, methoxyacetyl-, azetidine-1-carbonyl-, methoxycarbonyl-, ethoxycarbonyl-, dimethylaminocarbonyl-, methanesulfonyl-, ethane-2-sulfonyl-, propane-2-sulfonyl-, azetidin-1-yl-sulfonyl-, dimethylaminosulfonyl-, $N^1$-azetidin-1-yl-$N^2$-cyano-amidino-, and $N^2$-cyano-$N^1$,$N^1$-dimethyamidino-).

In certain embodiments, $R_{1.3}$ is optionally substituted pyridinyl, optionally substituted imidazolyl, nitro, or halo;

n is 2; and $R_3$ is chosen from optionally substituted acyl, optionally substituted alkoxycarbonyl, amidino, and sulfonyl (such as acetyl, methoxyacetyl-, azetidine-1-carbonyl-, methoxycarbonyl-, ethoxycarbonyl-, dimethylaminocarbonyl-, methanesulfonyl-, ethane-2-sulfonyl-, propane-2-sulfonyl-, azetidin-1-yl-sulfonyl-, dimethylaminosulfonyl-, $N^1$-azetidin-1-yl-$N^2$-cyano-amidino-, and $N^2$-cyano-$N^1$,$N^1$-dimethyamidino-).

In certain embodiments, $R_{1.3}$ is pyridinyl or fluoro;

n is 2; and $R_3$ is chosen from optionally substituted acyl, optionally substituted alkoxycarbonyl, amidino, and sulfonyl (such as acetyl, methoxyacetyl-, azetidine-1-carbonyl-, methoxycarbonyl-, ethoxycarbonyl-, dimethylaminocarbonyl-, methanesulfonyl-, ethane-2-sulfonyl-, propane-2-sulfonyl-, azetidin-1-yl-sulfonyl-, dimethylaminosulfonyl-, $N^1$-azetidin-1-yl-$N^2$-cyano-amidino-, and $N^2$-cyano-$N^1$,$N^1$-dimethyamidino-).

In certain embodiments, $R_{1.3}$ is fluoro;

n is 2; and $R_3$ is chosen from optionally substituted acyl, optionally substituted alkoxycarbonyl, amidino, and sulfonyl (such as acetyl, methoxyacetyl-, azetidine-1-carbonyl-, methoxycarbonyl-, ethoxycarbonyl-, dimethylaminocarbonyl-, methanesulfonyl-, ethane-2-sulfonyl-, propane-2-sulfonyl-, azetidin-1-yl-sulfonyl-, dimethylaminosulfonyl-, $N^1$-azetidin-1-yl-$N^2$-cyano-amidino-, and $N^2$-cyano-$N^1$,$N^1$-dimethyamidino-).

In certain embodiments, $R_{1.3}$ is optionally substituted pyridinyl, optionally substituted imidazolyl, nitro, or halo;

n is 1; and $R_3$ is acetyl or dimethylaminosulfonyl-.

In certain embodiments, $R_{1.3}$ is pyridinyl or fluoro;

n is 1; and $R_3$ is acetyl or dimethylaminosulfonyl-.

In certain embodiments, $R_{1.3}$ is fluoro;

n is 1; and $R_3$ is acetyl or dimethylaminosulfonyl-.

In certain embodiments, $R_{1.3}$ is optionally substituted pyridinyl, optionally substituted imidazolyl, nitro, or halo;

n is 2; and $R_3$ is acetyl or dimethylaminosulfonyl-.

In certain embodiments, $R_{1.3}$ is pyridinyl or fluoro;

n is 2; and $R_3$ is acetyl or dimethylaminosulfonyl-.

In certain embodiments, $R_{1.3}$ is fluoro;

n is 2; and $R_3$ is acetyl or dimethylaminosulfonyl-.

EXAMPLES

The following examples are given to enable those skilled in the art to more clearly understand and to practice the present invention. They should not be considered as limiting the scope of the invention, but merely as being illustrative and representative thereof. The syntheses reported in the examples were performed in the laboratories of IRIX Pharmaceuticals, Inc. (Florence, S.C.).

Example 1

(R)-1-[3-(1-Acetyl-piperidin-3-yloxy)-5-fluoro-phenyl]-3-pyridin-3-yl-urea

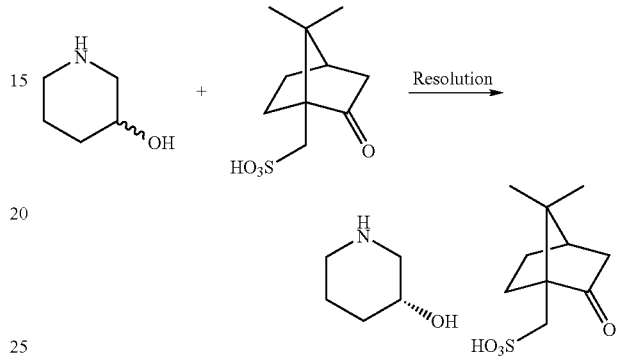

(The amounts listed below are the total amounts used; therefore, ¼ of the total amount was added to each 50 L flask.)

1A. (R)-3-Hydroxypiperidine (S)-1-(+)-camphor-10-sulfonate salt

Four 50 L 3-neck RBF extractors equipped with a mechanical stirrer under nitrogen, were charged with 10.76 kg (46.14 mol) (S)-1-(+)-camphor-10-sulfonic acid, 23.3 L (2.5 vol) ethanol (absolute), and 9.34 kg (92.27 mol) 3-hydroxypiperidine. The solution was then brought to turbidity with the addition of 142 L MTBE. The solution was stirred overnight, and the solids were filtered and rinsed with 8 L (1:1) MTBE:EtOH, 8 L (2:1) MTBE:EtOH, and 8 L MTBE to afford 10.68 kg white solid (35% yield, 75.8% ee, these numbers are an average of the two lots). These solids were charged to a 22 L 3-neck RBF fitted with a mechanical stirrer, thermometer, and reflux condenser. The flasks were charged with 10.7 L (1 vol) ethanol (absolute), and the solution was warmed to 55° C. The heat was turned off, and the solution cooled to room temperature overnight. The solids were filtered and rinsed with 1.5 L (2×) (1:1) MTBE:EtOH, and 3 L (2×) MTBE to afford 6.95 kg of (R)-3-hydroxypiperidine (S)-1-(+)-camphor-10-sulfonate salt as a white solid in 22.6% yield (theoretical yield=30.79 kg, purity=97.2% ee).

1B. 1-((R)-3-Hydroxy-piperidin-1-yl)-ethanone

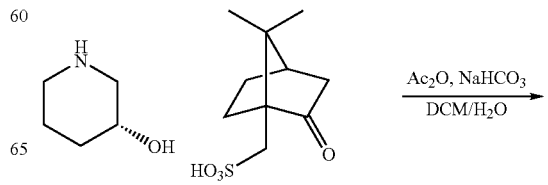

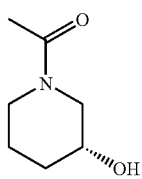

(The amounts listed below are the total amounts used; therefore, a proportional amount was added to each flask: ½ to the 50 L and ¼ to each 22 L extractors.)

One 50 L and two 22 L extractors equipped with mechanical stirrers, stoppers, and nitrogen bubblers were purged with nitrogen for at least ten minutes. The extractors were charged with 3.21 kg (38.21 mol) sodium bicarbonate and 27.9 L (4 vol) water. (R)-3-Hydroxypiperidine (S)-1-(+)-camphor-10-sulfonate salt 6.95 kg (20.84 mol) was charged to the extractors, followed by the addition of 27.9 L (4 vol) dichloromethane. The solutions were stirred for 30 min, then 2.36 L (25.0 mol) acetic anhydride was added portion-wise for 2 hours to ensure slow off-gassing. The reaction was allowed to stir overnight and was deemed complete by TLC analysis of the aqueous and organic layers (100% methanol/ ninhydrin stain). The reaction was concentrated, and 28 L toluene was used to assist the water removal. Once the solid was dry, it was divided between two 20 L round bottom flasks (5.8 kg/flask). 24 L (1:1) MTBE: DCM, 8 kg (1.2 mass eq) sodium sulfate, and 4 kg (47.61 mol) sodium bicarbonate were added, and the solution was stirred overnight (without vacuum). The solids were filtered and rinsed with 24 L (12 L per flask) dichloromethane. The filtrates were split into 4 L quantities per 20 L carboys and diluted with 1690 L (8 L per carboy) MTBE. The solutions sat for 12 hours, and the precipitated solids were filtered and concentrated to afford 2.92 kg 1-((R)-3-hydroxy-piperidin-1-yl)-ethanone in 98% yield as a yellow oil (theoretical yield=2.98 kg, purity=95.2% and 97.4% ee).

1C. 1-[(R)-3-(3-Fluoro-5-nitro-phenoxy)-piperidin-1-yl]-ethanone and 1-[(R)-3-(3, 5-Difluoro-phenoxy)-piperidin-1-yl]-ethanone

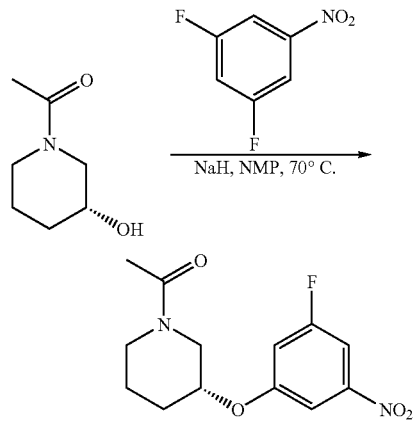

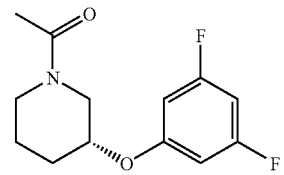

(The amounts listed below are the total amounts used; therefore, ½ of the total amount was added to each 22 L flask.)

Two 22 L 3-neck RBFs equipped with cooling baths, mechanical stirrers, thermowells, y-adapters, rubber septa, and nitrogen bubblers were purged with nitrogen for at least ten minutes. The flasks were charged with 0.884 kg (22.1 mol) sodium hydride (0.442 kg apiece) and 4.86 L (2 vol) NMP (2.43 L apiece). The flasks were cooled to 0±5° C. in an ice/brine bath. A solution of 2.43 kg (17 mol) 1-((R)-3-hydroxy-piperidin-1-yl) -ethanone (1.22 kg apiece) and 0.058 kg (0.85 mol) imidazole (0.029 kg apiece) in 4.86 L (2 vol) NMP (2.43 L apiece) was added dropwise over 1.5 hours to the flask, maintaining an internal temperature below 5±5° C. The solution stirred for 2 hours, then was cannulated into two 22 L 3-neck RBFs equipped with cooling baths, mechanical stirrers, thermowells, y-adapters, rubber septa, and nitrogen bubblers that were purged with nitrogen for at least ten minutes and charged with a solution of 2.70 kg (16.97 mol) 3,5-difluoronitrobenzene (1.35 L apiece) in 2.43 L (1 vol) NMP (1.22 L apiece) that was cooled to 0±5° C. in an ice/brine bath. The cannulation lasted for 2 hours, maintaining an internal temperature below 10±5° C. The solution was warmed to 70±5° C. for 11 hours, and was deemed complete by TLC (1:1 hexanes:acetone/PMA stain) and GC. The solution was cooled and poured into four 50 L extractors with 54 L MTBE and 54 L water. The layers were separated, and the aqueous layer was reextracted with 54 L MTBE. The combined organic layers were washed with 54 L (3×) water and 54 L brine. The organics were dried over sodium sulfate, filtered and concentrated to afford 4.54 kg of a mixture of 1-[(R)-3-(3-fluoro-5-nitro-phenoxy)-piperidin-1-yl]-ethanone and 1-[(R)-3-(3,5-difluoro-phenoxy)-piperidin-1-yl]-ethanone in 95% yield (theoretical yield=4.79 kg, purity=83.2% 1-[(R)-3-(3-fluoro-5-nitro -phenoxy)-piperidin-1-yl]-ethanone and 9.2% 1-[(R)-3-(3,5-difluoro-phenoxy)-piperidin-1-yl]-ethanone and 98.0% ee).

1 D. 1-[(R)-3-(3-Amino-5-fluoro-phenoxy)-piperidin-1-yl]-ethanone

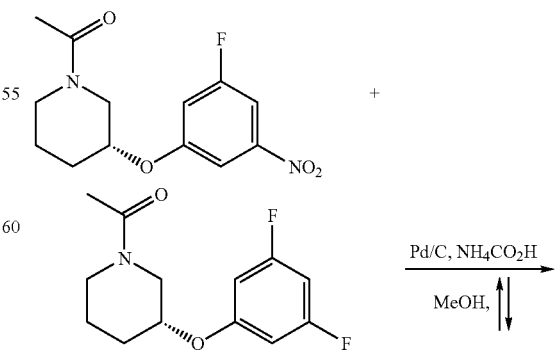

-continued

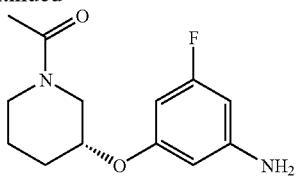

(The amounts listed below are the total amounts used; therefore, ⅓ of the total amount was added to each 22 L flask.)

Three 22 L 3-neck RBFs equipped with heating mantles, mechanical stirrers, thermowells, condensers, and nitrogen bubblers were purged under nitrogen for at least ten minutes. The flasks were charged with 0.454 kg (10 wt %) Pd/C, and 13.62 L (3 vol) methanol. A solution of 4.54 kg (~16.1 mol) of a mixture of 1-[(R)-3-(3-fluoro-5-nitro-phenoxy) -piperidin-1-yl]-ethanone and 1-[(R)-3-(3,5-difluoro-phenoxy)-piperidin-1-yl]-ethanone in 4.54 L (1 vol) methanol was then charged to the flasks, and an additional 4.54 L (1 vol) methanol was added to the flasks. The solutions were warmed to a gentle reflux, and a solution of 5.07 kg (80.4 mol) ammonium formate in 3.63 L water was then added drop-wise for 10 hours. The reactions were deemed complete by TLC (1:1 hexanes:acetone/PMA stain) and HPLC, and were filtered through celite and concentrated. The concentrate was transferred to two 50 L extractors, and was partitioned between 47.2 L MTBE and 17.7 L 3N HCl. The layers were separated, and the organics were extracted with 6 L (2×) 3N HCl. The aqueous layers were neutralized with 3.54 kg NaOH to pH ~7, then 9.6 L saturated sodium bicarbonate was added. The aqueous layers were then extracted with 6 L (3×) DCM. The combined organics were washed with 18 L brine, dried over sodium sulfate, filtered and concentrated to yield 3.06 kg of 1-[(R)-3-(3-amino-5-fluoro-phenoxy)-piperidin-1-yl]-ethanone in 75% yield as a thick brown oil (theoretical yield=4.06 kg, purity=90.7% and 95.4% ee).

1E. 1-[(R)-3-(3-Amino-5-fluoro-phenoxy)-piperidin-1-yl]-ethanone HCl salt

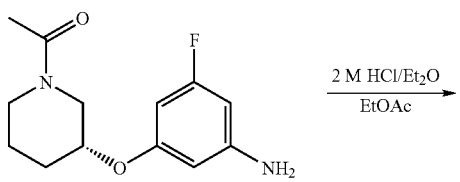

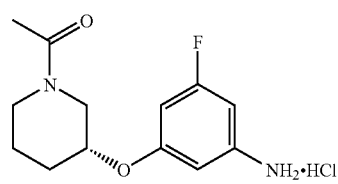

A 22 L 3-neck RBF equipped with a cooling bath, an addition funnel, mechanical stirrer, thermocouple and nitrogen bubbler was purged with nitrogen for at least ten minutes. The flask was charged with 0.612 kg (2.43 mol) 1-[(R)-3-(3-amino-5-fluoro-phenoxy) -piperidin-1-yl]-ethanone and 12.2 L (20 vol) ethyl acetate. The solution was cooled to 0±5° C. in an ice/brine bath, and 1.46 L (2.92 mol) 2M HCl in ether was added dropwise for 20 minutes, maintaining the internal temperature below 10° C. The solution stirred for 2 hours at 0±5° C., and the solid was filtered under a nitrogen atmosphere and rinsed with 6.0 L (10 vol) ethyl acetate. The solid was dried at 50±5° C. under vacuum for 2 days to afford 693 g of 1-[(R)-3-(3-amino-5-fluoro-phenoxy)-piperidin-1-yl]-ethanone HCl salt in 99% yield as an off-white solid (theoretical yield=0.700 kg, purity=94.2% and 97.6% ee).

1F. (R)-1-[3-(1-Acetyl-piperidin-3-yloxy)-5-fluoro-phenyl]-3-pyridin-3-yl-urea

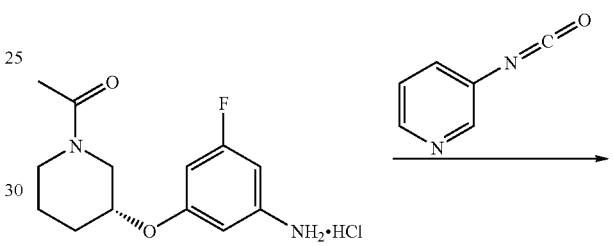

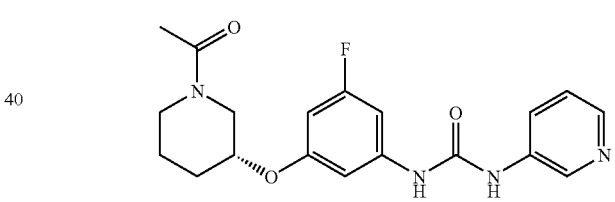

A 22 L 3-neck RBF equipped with a cooling bath, mechanical stirrer, thermocouple, and nitrogen bubbler was purged with nitrogen for at least ten minutes. The flask was charged with 1.441 kg (4.990 mol) 1-[(R)-3-(3-amino-5-fluoro-phenoxy)-piperidin-1-yl]-ethanone HCl salt and 14.4 L (10 vol) dichloromethane. The solution was stirred, and 0.710 kg (5.489 mol) DIPEA was charged. The solution was cooled to 10±5° C. in an ice/brine bath. The reaction was charged with 0.659 kg (5.489 mol) 3-isocyanato-pyridine and the solution warmed to room temperature and stirred for three hours. The reaction was monitored by TLC (1:9 methanol:ethyl acetate/PMA stain) and HPLC. The reaction stirred at room temperature for five more hours, and another 0.009 kg (0.075 mol) 3-isocyanato-pyridine was added. The solution stirred for 15 more hours, and the reaction was deemed complete. The solution was poured into a 50 L extractor containing 14.4 L (10 vol) saturated sodium bicarbonate, and the flask was rinsed with an additional 1.44 L (1 vol) dichloromethane. The layers were separated, and the organic layer was washed with 14.4 L (2×10 vol) water. The organic layer was dried with 1.69 kg sodium sulfate for at least 20 minutes before proceeding to the next step.

1G. Purification of (R)-1-[3-(1-acetyl-piperidin-3-yloxy)-5-fluoro-phenyl]-3-pyridin-3-yl-urea.

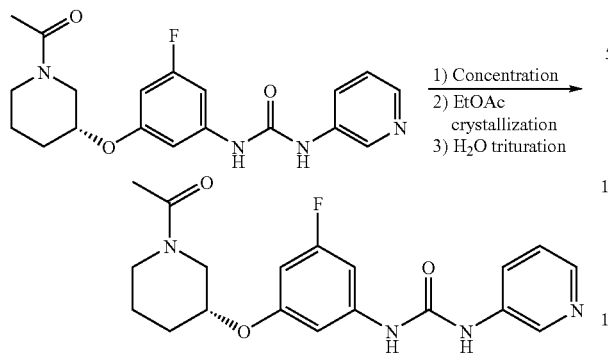

The DCM mixture from Example 1F was concentrated at 35±5° C. under reduced pressure until condensation ceased, then for one hour longer at 45∓5° C. The contents were transferred to a 22 L 3-neck RBF equipped with a heating mantle, condenser, mechanical stirrer, thermocouple, and nitrogen bubbler that had been purged with nitrogen for at least ten minutes. The rotovap flask was rinsed with 14.5 L ethyl acetate, and the rinse was poured into the 22L 3-neck RBF. The solution was warmed to 55±5° C., then was cooled to room temperature for ten minutes. The suspension was then heated to 60±5° C. for an hour. The heater was turned off and the solution gradually cooled to room temperature. The solids were filtered and washed with 8.7 L ethyl acetate. The crystals were dried at 45±5° C. for 13.5 hours. The crystals were then transferred to a 22 L 3-neck RBF equipped with a heating mantle, condenser, mechanical stirrer, thermocouple, and nitrogen bubbler that had been purged with nitrogen for at least ten minutes. The flask was then charged with 14.5 L water, and the suspension was heated to 50±5° C. for 34 hours. The solid was filtered and dried under vacuum at 45±5° C. to afford 2.46 kg of an off-white solid. The crystals were then transferred to a 22 L 3-neck RBF equipped with a heating mantle, condenser, mechanical stirrer, thermocouple, and nitrogen bubbler that had been purged with nitrogen for at least ten minutes. 11.6 L water was then charged, and the solution was warmed to 50±5° C. for 5 hours. The heat was turned off, and the solution was allowed to cool to room temperature. The solution was warmed to 50±5° C. for a second cycle of 20 hours. The solids were filtered and rinsed with 14.5 L water. They were then charged to a 22 L 3-neck RBF equipped with a heating mantle, condenser, mechanical stirrer, thermocouple, and nitrogen bubbler that had been purged with nitrogen for at least ten minutes, and 12.5 L water was added. The solution was warmed to 50±5° C. for 5.5 hours. The crystals were filtered and rinsed with 14.5 L water, and dried under vacuum at 50±5° C. to afford 2.38 kg off-white solid. The solid was then taken up in 8 L water, and was concentrated on the rotovap with a bath temperature of 50±5° C. 16 L Water was added to the flasks portionwise, and the solids were filtered and rinsed with 15.5 L water. The crystals were dried under vacuum at 50±5° C. to afford 2.28 kg of the purified title compound, (R)-1-[3-(1-acetyl-piperidin-3-yloxy)-5-fluoro-phenyl]-3-pyridin-3-yl -urea in 61% yield as an off-white solid (mp=145° C., theoretical yield=3.74 kg, purity=98.7% and 99.2% ee).

Example 2

(R)-3-[3-Fluoro-5-(3-pyridin-3-yl-ureido)-phenoxy]-pyrrolidine-1-sulfonic acid dimethylamide

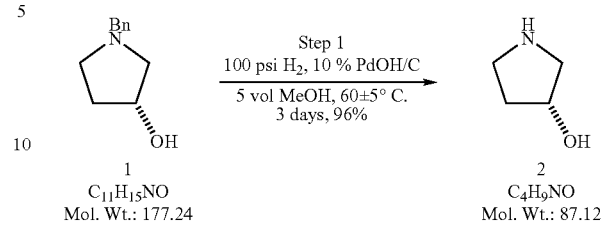

Step 1
100 psi $H_2$, 10 % PdOH/C
5 vol MeOH, 60±5° C.
3 days, 96%

1
$C_{11}H_{15}NO$
Mol. Wt.: 177.24

2
$C_4H_9NO$
Mol. Wt.: 87.12

Two 8 L Parr reactors were purged with nitrogen, and charged with (0.25 kg, 10 wt %) 20% PdOH/C. The system was once more purged with nitrogen and placed under vacuum. A solution of (2.50 kg, 14.1 mol) 3-hydroxypyrrolidine (1) in (15.3 L, 4.5 vol) MeOH was then charged and the system was purged with nitrogen once more. The solution was then placed under an atmosphere of hydrogen (100 psi) and warmed to 60±° C. and stirred for three days and was deemed complete by GC & TLC analysis (20% methanol/DCM, ninhydrin stain). The reactors were emptied and rinsed with 4 L MeOH. The reaction mixture and reactor rinses were filtered through celite and concentrated to afford 1.18 kg of 2 in 96% yield (theoretical yield=1.23 kg, GC purity=97.1%).

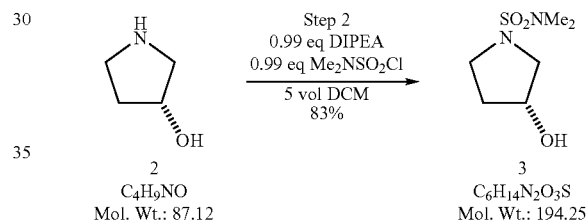

Step 2
0.99 eq DIPEA
0.99 eq $Me_2NSO_2Cl$
5 vol DCM
83%

2
$C_4H_9NO$
Mol. Wt.: 87.12

3
$C_6H_{14}N_2O_3S$
Mol. Wt.: 194.25

A 22 L 3-neck RBF was equipped with a cooling bath, mechanical stirrer, thermowell, 1 L addition funnel, and nitrogen bubbler and purged with nitrogen for at least ten minutes. The flasks were charged with (1.15 kg, 12.81 mol, moles of 2 corrected for 97.3% GC purity) compound 2 and (21.1 L, 5 vol) DCM (2.43 L apiece). The flasks were cooled to 0±5° C. in an ice/brine bath, and (2.21 L, 12.43 mol/0.97 eq) DIPEA was added. The addition funnel was then charged with (1.35 L, 12.43 mol/0.97 eq) dimethylsulfamoyl chloride, which was the added dropwise for 3 hours, maintaining an internal reaction temperature <10° C. ($T_{max}$=9.8° C.). The solution stirred for 30 minutes and was incomplete by TLC (1:1 ACN:EtOH, 5% AcOH, ninhydrin stain). After stirring for another 30 min (1 hr total), (0.13 mol) DIPEA and (0.13 mol) dimethylsulfamoyl chloride was added. The reaction stirred for another hour, and was incomplete by TLC. (0.13 mol) DIPEA and (0.13 mol) dimethylsulfamoyl chloride was added. The reaction stirred for 20 hours and 20 min., and was deemed complete by GC & TLC analysis (1:1 ACN:EtOH, 5% AcOH, ninhydrin stain). The solution was poured into a 40 L extractor and rinsed with DCM. The organics were washed with water, which was back-extracted with DCM. The combined organics were washed with (2×) water and (2×) 1:1 water:brine and brine. The organics were dried over sodium sulfate, filtered and concentrated to afford 1.17 kg of 3 in 46% yield (theoretical yield=2.56 kg, purity=94.0%). The aqueous layers were then combined and brought to pH 4 with (0.08 mol) conc. HCl and extracted with (4×) EtOAc. The combined organics were washed with brine, dried over sodium sulfate, and concentrated to afford 0.61 kg of 3 in 24% yield (theoretical yield=2.56 kg, purity=99.7%). The aqueous layers were then combined and extracted with (3×) DCM. The combined organics were washed with water and brine, dried over sodium sulfate, and concentrated to afford 0.34 kg of 3 in 13% yield (theoretical yield=2.56 kg, purity=99.7%).

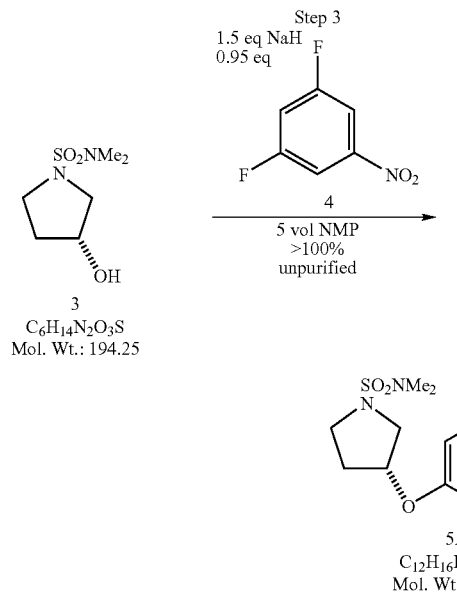

A 22 L 3-neck RBFs was equipped with a cooling bath, mechanical stirrer, addition funnel, thermowell, and nitrogen bubbler and was purged with nitrogen for at least ten minutes. The flask was then charged with (1938.8 g, 9.95 mol, moles of 3 corrected for 99.7% GC purity) of compound 3, (9.7 L, 5 vol) NMP, and (33.9 g, 0.05 mol) imidazole. The flask was cooled to 0±5° C. in an ethylene glycol bath, and 597.1 g, 14.93 mol) sodium hydride was added portionwise, keeping T<10° C. The reaction was then cooled to ⁻22° C., and (1.07 L, 9.45 mol) 3,5-difluoronitrobenzene was added dropwise for 2.5 hours, maintaining an internal temperature <⁻20±5° C. The reaction stirred for 8.5 hours and was deemed complete by GC & TLC analysis (100% EtOAc, PMA stain). The solution was the cooled to ⁻10° C. and was quenched with 0.5 L water. The solution was then poured into 30 L MTBE and 27.5 L water. The layers were separated, and the aqueous layer was back-extracted with 30 L MTBE. The combined organic layers were washed with (3×) water and 15 L brine. The organics were dried over sodium sulfate, filtered and concentrated to afford 3.35 kg of 5A in 101% unpurified yield (theoretical yield=3.31 kg, purity=GC-90.5%, LC-92.1% @ 215 nm and 93.3% @ 254 nm).

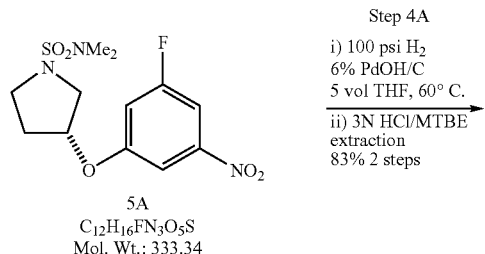

-continued

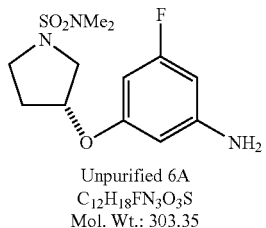

Unpurified 6A
C₁₂H₁₈FN₃O₃S
Mol. Wt.: 303.35

A 60 L reactor was charged with (0.40 kg, 5.7 wt %) 20% PdOH/C, followed by a solution of (7.03 kg, 21.1 mol) of compound 5A in (35 L, 5 vol) THF. The solution was vigorously stirred, and placed under an atmosphere of 60 psi H₂. Cooling water was passed through the cooling coils to maintain an internal reaction temperature ≦60° C. for the initial 2 hours, then the reactor slowly cooled to room temperature. After stirring for 87 hours, the reaction was deemed complete by TLC (1:1 EtOAc:Hex & 9:1 DCM: ACN, PMA stain) and HPLC. The reactor was emptied and rinsed with (4 L, 6×) THF. The reaction mixture and reactor rinses were filtered through celite and rinsed with 10 L MeOH. The organics were concentrated then taken up in 64 L MTBE and extracted with (39.2 L, 1×19.2, then 2×10 L) 3N HCl. The aqueous layers were then neutralized to pH~7 with solid NaOH and extracted with (2×13 L) DCM. The combined organics were washed with brine, dried over sodium sulfate, filtered and concentrated to afford 5.32 kg of 6A in 82% yield for 2 steps (theoretical yield=6.48 kg for 2 steps, purity=89.5% @ 215 and 91.0% @ 254).

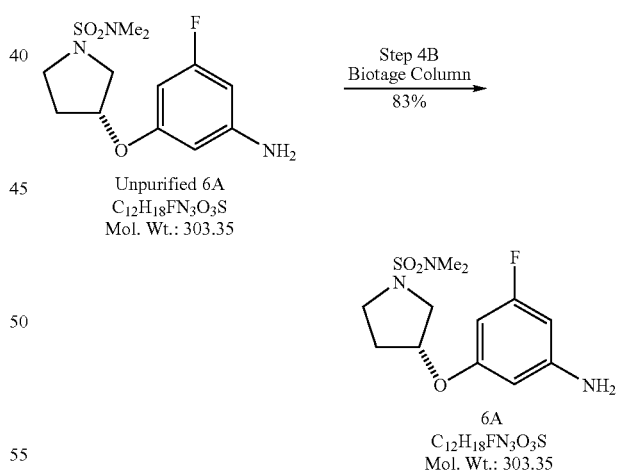

A solution of 0.70 kg of unpurified compound 6A in 0.325 L DCM was charged to a Biotage Flash 150 column, and the charging chamber was rinsed with 2.0 L DCM. Four liter fractions were collected while passing 16 L DCM through to the column, followed by 48 L of 15% ACN/DCM. The column was flushed with 48 L THF, followed by 16 L DCM. This representative procedure was repeated 5 times to provide 2.61 kg of compound 6A (99.9% @ 215 nm and 99.8% @ 254 nm).

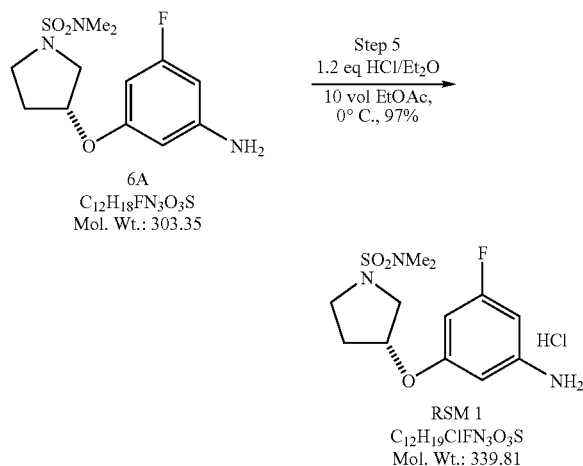

A 22 L 3-neck RBF equipped with a cooling bath, addition funnel, mechanical stirrer, thermocouple and nitrogen bubbler was purged with nitrogen for at least ten minutes. The flask was charged with (0.976 kg, 3.20 mol) of compound 6A and (9.7 L, 10 vol) EtOAc. The solution was cooled to 0±5° C. in an ice/brine bath, and (1.92 L, 3.84 mol) 2M HCl in ether was added dropwise for 3 hours, maintaining an internal temperature <10° C. The solution stirred for 30 minutes at 0±5° C., and the solid was filtered and rinsed with (4.9 L, 5 vol) EtOAc. The solid was dried at 50±5° C. under vacuum for 2 days to afford 1.06 kg RSM 1 in 97% yield as an off-white solid (theoretical yield=1.09 kg, purity=99.3% @ 215 nm and 99.1% @ 254 nm).

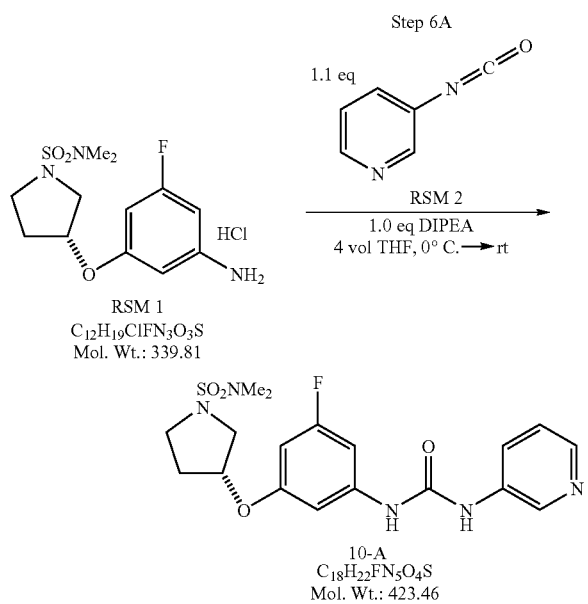

A 22 L 3-neck RBF equipped with a cooling bath, mechanical stirrer, thermocouple, and nitrogen bubbler was purged with nitrogen for at least ten minutes. The flask was charged with (1.355 kg, 3.988 mol) RSM 1 and (5.4 L, 4 vol) THF. The solution was stirred, and (0.70 L, 3.988 mol) DIPEA was charged. The solution was cooled to 0±5° C. in an ice/brine bath. The reaction was charged with (0.479 kg, 3.988 mol) RSM 2. and the ice/brine cooling bath was removed to allow the reaction to warm to room temperature. The reaction stirred for four hours at room temperature and was deemed incomplete by TLC (1:9 ACN/DCM, PMA stain) and HPLC. (0.024 kg, 0.20 mol, 0.05 eq) RSM 2 was added, and the solution stirred for 15 more hours at room temperature and was deemed incomplete. (0.019 kg, 0.16 mol, 0.04 eq) RSM 2 was added, and the solution stirred for another hour before being deemed complete. The reaction was poured into (5.4 L, 4 vol) water, and (5.4 L, 4 vol) EtOAc. The layers were separated, and the aqueous layer was back extracted with (5.4 L, 4 vol) EtOAc. The organic layers were washed with (8.1 L, 3×2 vol) 0.1 N HCl, checking the symmetrical urea percentage in the organic layer after each wash. The organics were then washed with (5.4 L, 4 vol) 1:1 saturated sodium bicarbonate:brine, then (5.4 L, 4 vol) brine. The extractors were rinsed with (1.4 L, 1 vol) EtOAc. The organics were then dried over sodium sulfate before proceeding to the next step.

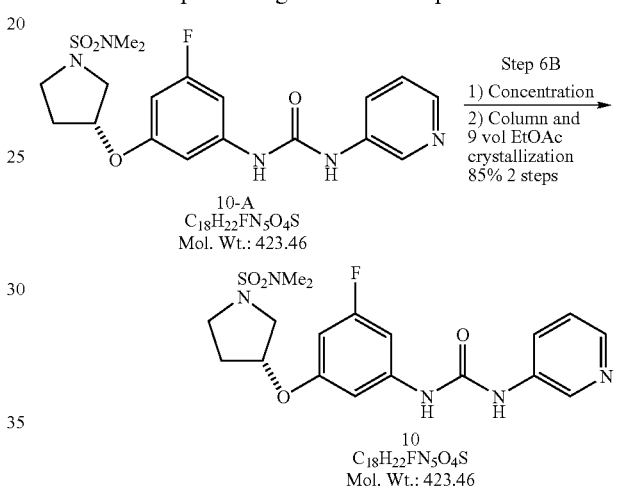

Compound 10-A in EtOAc/THF was concentrated at ≦55° C. under reduced pressure until condensation ceased, then the contents were transferred to a 22 L 3-neck RBF equipped with a heating mantle, condenser, mechanical stirrer, thermocouple, and nitrogen bubbler that had been purged with nitrogen for at least ten minutes. The rotovap flask was rinsed with 12.0 L EtOAc, and the rinse was poured into the 22 L 3-neck RBF. The solution was warmed to 55±5° C., then was cooled to room temperature and allowed to stir for 3 hours. The suspension was then heated to 55±5° C., then was cooled to room temperature and allowed to stir for 12 hours. The solids were filtered and washed with (16.3 L, 6 vol based on RSM 1) EtOAc. The crystals were dried at ≦55° C. for 2 days to afford 2.88 kg of Compound 10 in 85% yield as a white solid (theoretical yield=3.38 kg, purity=99.3% @ 254 nm & 99.6% @ 215 nm and 100% e.e.).

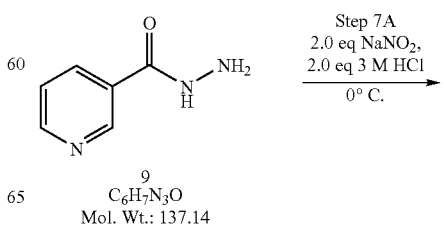

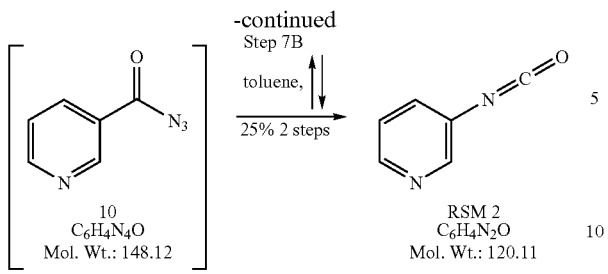

A 22 L 3-neck RBF equipped with a cooling bath, mechanical stirrer, thermocouple, addition funnel, and nitrogen bubbler was purged with nitrogen. The flask was charged with (5.80 L, 17.5 mol) 3 M HCl and was cooled to 0±5° C. in an ice/brine bath. (1.20 kg, 8.75 mol) 9 was added portion-wise for 20 minutes, maintaining the internal temperature ≦0° C. A solution of (1.21 kg, 17.5 mol) NaNO$_2$ in 2.4 L water was added dropwise for 3 hours, maintaining the internal temperature at 0±5° C. Once the addition was complete, the reaction was deemed complete by TLC (1:4 MeOH:DCM/ninhydrin). The reaction was neutralized with (1.25 kg, ~1 mass eq) sodium bicarbonate, and was diluted with 3L water and 2.5 L toluene The layers were separated, and the aqueous layers were extracted with (2L, 2×) toluene. The toluene layers were combined and washed with 2L saturated sodium bicarbonate and 2L brine. The toluene layers were then dried over sodium sulfate. The aqueous layers were then extracted with (2L, 3×) MTBE, and the combined organic layers were washed with 2L water and 2L brine. The MTBE layers were dried over sodium sulfate, filtered, concentrated, and combined with the toluene layers and carried through to the next step.

A 22 L 3-neck RBF equipped with a mechanical stirrer, thermocouple, condenser, and nitrogen bubbler was purged with nitrogen and charged with 2.5 L toluene and warmed to reflux. The toluene solution of 10 was then added dropwise over 14 hours. The solution stirred at reflux for 15 min, and was deemed complete by TLC (1:1 hexanes:acetone/PMA). The toluene was distilled under a nitrogen stream, followed by RSM 2, which was collected from 120° C. to 150° C. to afford 1.07 kg of RSM 2 as a yellow solid in 25% yield for the two step process (theoretical=4.20 kg).

While certain embodiments have been shown and described, various modifications and substitutions may be made thereto without departing from the spirit and scope of the invention. Accordingly, it is to be understood that the present invention has been described by way of illustration and not limitations.

What is claimed:

1. A method for the synthesis of an enantiomerically pure compound of Formula I:

Formula I

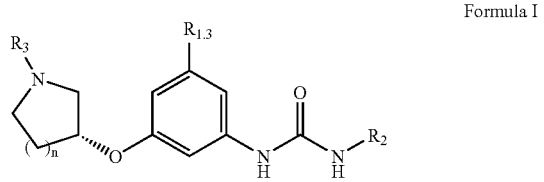

where:
R$_{1.3}$ is chosen from hydrogen, halo, optionally substituted heteroaryl, and nitro;

R$_2$ is chosen from optionally substituted aryl, optionally substituted aralkyl, optionally substituted cycloalkyl, optionally substituted heteroaryl, optionally substituted heteroaralkyl, and optionally substituted heterocyclyl;

R$_3$ is chosen from optionally substituted acyl, optionally substituted alkoxycarbonyl, amidino, and sulfonyl; and n is 1 or 2, wherein the method comprises at least one of the steps:

A) contacting a base with an enantiomerically pure compound of Formula 101:

101

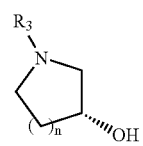

B) reacting the product of step A with a compound of Formula 102:

102

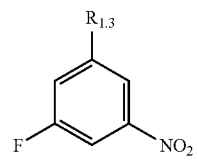

and

C) converting the product of step B to the compound of Formula I.

2. The method of claim 1 wherein the step of converting the product of step B to the compound of Formula I, comprises the steps of:

D) reducing the product of step B to the corresponding amine of Formula 105:

105

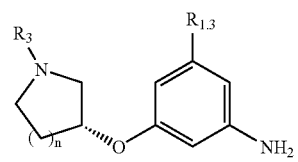

and

E) reacting the product of step D with a compound of the formula O═C═N—R$_2$ wherein R$_2$ is chosen from optionally substituted aryl, optionally substituted aralkyl, optionally substituted cycloalkyl, optionally substituted heteroaryl, optionally substituted heteroaralkyl, and optionally substituted heterocyclyl.

3. The method of claim 2 wherein R$_{1.3}$ is optionally substituted heteroaryl, nitro or halo.

4. The method of claim 3 wherein R$_{1.3}$ is optionally substituted pyridinyl, optionally substituted imidazolyl, nitro, or halo.

5. The method of claim 4 wherein R$_{1.3}$ is pyridinyl or fluoro.

6. The method of claim 5 wherein R$_{1.3}$ is fluoro.

7. The method of claim 2, wherein R$_2$ is optionally substituted phenyl, optionally substituted naphthyl, optionally substituted pyrrolyl, optionally substituted, thiazolyl, optionally substituted isooxazolyl, optionally substituted pyrazolyl, optionally substituted pyridinyl, optionally substituted pyrazinyl, optionally substituted pyrimidinyl, or optionally substituted pyridazinyl.

8. The method of claim 7 wherein $R_2$ is isooxazol-3-yl, 5-methyl-isooxazol-3-yl, isooxazol-5-yl, pyrazol-3-yl, pyrazinyl, substituted phenyl or optionally substituted pyridinyl.

9. The method of claim 8 wherein $R_2$ is pyridin-3-yl optionally p-substituted with a member of the group: acetyl, methyl, ethyl, methoxy, methoxymethyl, hydroxy, hydroxymethyl and hydroxyethyl.

10. The method of claim 9 wherein $R_2$ is pyridin-3-yl or 6-methyl-pyridin-3-yl.

11. The method of claim 1, wherein $R_3$ is chosen from acetyl, methoxyacetyl-, azetidine-1-carbonyl-, methoxycarbonyl-, ethoxycarbonyl-, dimethylaminocarbonyl-, methanesulfonyl-, ethane-2-sulfonyl-, propane-2-sulfonyl-, azetidin-1-yl-sulfonyl-, dimethylaminosulfonyl-, $N^1$-azetidin-1-yl-$N^2$-cyano-amidino-, and $N^2$-cyano-$N^1$,$N^1$-dimethyamidino-.

12. The method of claim 11 wherein $R_3$ is acetyl or dimethylaminosulfonyl-.

13. The method of claim 1, wherein n is 1.

14. The method of claim 1, wherein n is 2.

15. The method of claim 2, wherein the compound of Formula 105 has an enantiomeric excess of about 95% or more.

16. A method for the synthesis of an enantiomerically pure urea comprising the use, as a starting material, of an enantiomerically pure compound of Formula 101:

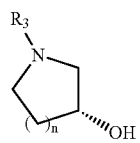

101 where:
$R_3$ is chosen from optionally substituted acyl, optionally substituted alkoxycarbonyl, amidino, and sulfonyl; and
n is 1 or 2.

17. The method of claim 16 further comprising the steps of:
A) contacting a compound of Formula 101 with a base, and
B) reacting the product of step A) with a compound of Formula 102 to yield a compound of Formula 103:

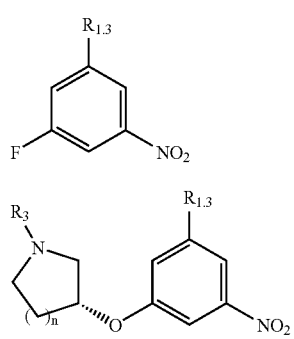

102

103 where
$R_{1.3}$ is chosen from hydrogen, halo, optionally substituted heteroaryl, and nitro.

18. The method of claim 17 further comprising the step of:
C) converting a compound of Formula 103 to a compound of Formula 105:

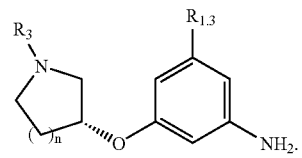

105

19. The method of claim 18 wherein the step of converting a compound of Formula 103 to a compound of Formula 105 comprises contacting a compound of Formula 103 with a catalyst and ammonium formate.

20. The method of claim 18 wherein the step of converting a compound of Formula 103 to a compound of Formula 105 comprises contacting a compound of Formula 103 with a catalyst and hydrogen gas.

21. The method of claim 18, further comprising the step of:
D) converting a compound of Formula 105 to a compound of Formula I:

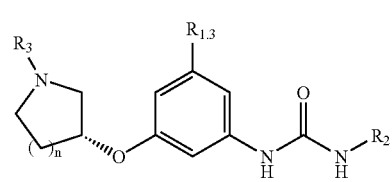

Formula I where:
$R_{1.3}$ is chosen from hydrogen, halo, optionally substituted heteroaryl, and nitro;
$R_2$ is chosen from optionally substituted aryl, optionally substituted aralkyl, optionally substituted cycloalkyl, optionally substituted heteroaryl, optionally substituted heteroaralkyl, and optionally substituted heterocyclyl,
$R_3$ is chosen from optionally substituted acyl, optionally substituted alkoxycarbonyl, amidino, and sulfonyl; and
n is 1 or 2.

22. The method of claim 21, wherein the step of converting a compound of Formula 105 to a compound of Formula I, comprises reacting a compound of Formula 105 with a compound of the formula $R_2$—NCO.

23. The method of claim 21 wherein the compound of Formula 105 is converted to the corresponding acid addition salt prior to reacting with a compound of the formula $R_2$—NCO.

24. The method of claim 17, wherein $R_{1.3}$ is optionally substituted heteroaryl, nitro or halo.

25. The method of claim 24 wherein $R_{1.3}$ is optionally substituted pyridinyl, optionally substituted imidazolyl, nitro, or halo.

26. The method of claim 25 wherein $R_{1.3}$ is pyridinyl or fluoro.

27. The method of claim 26 wherein $R_{1.3}$ is fluoro.

28. The method of claim 21, wherein $R_2$ is optionally substituted phenyl, optionally substituted naphthyl, optionally substituted pyrrolyl, optionally substituted, thiazolyl, optionally substituted isooxazolyl, optionally substituted pyrazolyl, optionally substituted pyridinyl, optionally substituted pyrazinyl, optionally substituted pyrimidinyl, or optionally substituted pyridazinyl.

29. The method of claim 28 wherein $R_2$ is isooxazol-3-yl, 5-methyl-isooxazol-3-yl, isooxazol-5-yl, pyrazol-3-yl, pyrazinyl, substituted phenyl or optionally substituted pyridinyl.

30. The method of claim 29 wherein $R_2$ is pyridin-3-yl optionally p-substituted with a member of the group: acetyl, methyl, ethyl, methoxy, methoxymethyl, hydroxy, hydroxymethyl and hydroxyethyl.

31. The method of claim 30 wherein $R_2$ is pyridin-3-yl or 6-methyl-pyridin-3-yl.

32. The method of claim 16, wherein $R_3$ is chosen from acetyl, methoxyacetyl-, azetidine-1-carbonyl-, methoxycarbonyl-, ethoxycarbonyl-, dimethylaminocarbonyl-, methanesulfonyl-, ethane-2-sulfonyl-, propane-2-sulfonyl-, azetidin-1-yl-sulfonyl-, dimethylaminosulfonyl-, $N^1$-azetidin-1-yl-$N^2$-cyano-amidino-, and $N^2$-cyano-$N^1,N^1$-dimethyamidino.

33. The method of claim 32 wherein $R_3$ is acetyl or dimethylaminosulfonyl-.

34. The method of claim 16, wherein n is 1.

35. The method of claim 16, wherein n is 2.

36. The method of claim 17, wherein the compound of Formula 103 has an enantiomeric excess of about 95% or more.

37. The method of claim 18, wherein the compound of Formula 105 has an enantiomeric excess of about 95% or more.

38. A composition comprising an enantiomerically pure compound of Formula I:

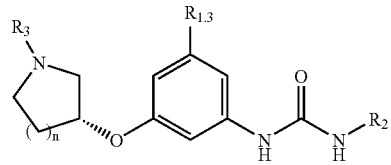

Formula I where:
  $R_{1,3}$ is chosen from hydrogen, halo, optionally substituted heteroaryl, and nitro;
  $R_2$ is chosen from optionally substituted aryl, optionally substituted aralkyl, optionally substituted cycloalkyl, optionally substituted heteroaryl, optionally substituted heteroaralkyl, and optionally substituted heterocyclyl;
  $R_3$ is chosen from optionally substituted acyl, optionally substituted alkoxycarbonyl, amidino, and sulfonyl; and
  n is 1 or 2, or a pharmaceutically acceptable salt thereof, having a detectable amount of at least one of the following:

A) a compound of Formula 104:

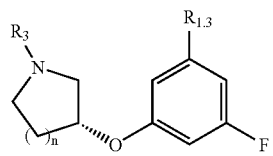

104

B) a compound of Formula 114:

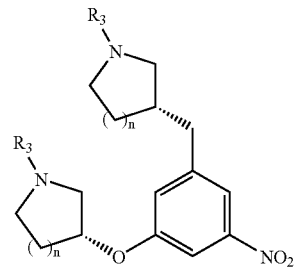

114

C) a compound of Formula 106:

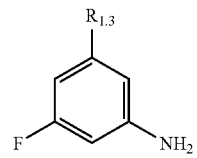

106

D) a compound of Formula 116:

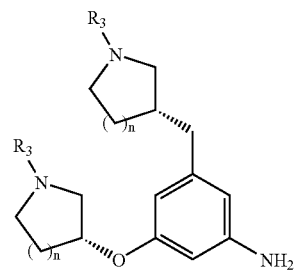

116

E) a compound of Formula 108:

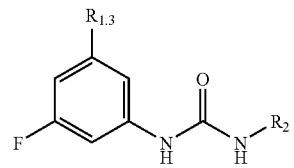

108

F) a compound of Formula 118:

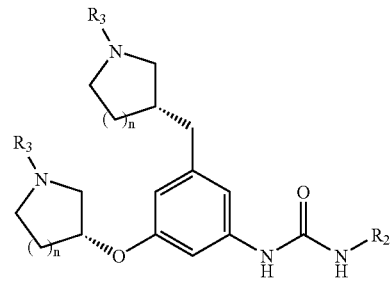

118

G) a compound of Formula 120:

$$R_2-NH-C(O)-NH-R_2 \qquad 120$$

and/or

H) a reagent employed in the synthesis of any of the foregoing.

39. The composition of claim 38 wherein $R_{1.3}$ is optionally substituted heteroaryl, nitro or halo.

40. The composition of claim 39 wherein $R_{1.3}$ is optionally substituted pyridinyl, optionally substituted imidazolyl, nitro, or halo.

41. The composition of claim 40 wherein $R_{1.3}$ is pyridinyl or fluoro.

42. The composition of claim 41 wherein $R_{1.3}$ is fluoro.

43. The composition of claim 38, wherein $R_2$ is optionally substituted phenyl, optionally substituted naphthyl, optionally substituted pyrrolyl, optionally substituted, thiazolyl, optionally substituted isooxazolyl, optionally substituted pyrazolyl, optionally substituted pyridinyl, optionally substituted pyrazinyl, optionally substituted pyrimidinyl, or optionally substituted pyridazinyl.

44. The composition of claim 43 wherein $R_2$ is isooxazol-3-yl, 5-methyl-isooxazol-3-yl, isooxazol-5-yl, pyrazol-3-yl, pyrazinyl, substituted phenyl or optionally substituted pyridinyl.

45. The composition of claim 44 wherein $R_2$ is pyridin-3-yl optionally p-substituted with a member of the group: acetyl, methyl, ethyl, methoxy, methoxymethyl, hydroxy, hydroxymethyl and hydroxyethyl.

46. The composition of claim 45 wherein $R_2$ is pyridin-3-yl or 6-methyl-pyridin-3-yl.

47. The composition of claim 38, wherein $R_3$ is chosen from acetyl, methoxyacetyl-, azetidine-1-carbonyl-, methoxycarbonyl-, ethoxycarbonyl-, dimethylaminocarbonyl-, methanesulfonyl-, ethane-2-sulfonyl-, propane-2-sulfonyl-, azetidin-1-yl-sulfonyl-, dimethylaminosulfonyl-, $N^1$-azetidin-1-yl-$N^2$-cyano-amidino-, and $N^2$-cyano-$N^1,N^1$-dimethylamidino-.

48. The composition of claim 47 wherein $R_3$ is acetyl or dimethylaminosulfonyl-.

49. The composition of claim 38, wherein n is 1.

50. The composition of claim 38, wherein n is 2.

51. An enantiomerically pure urea of Formula I

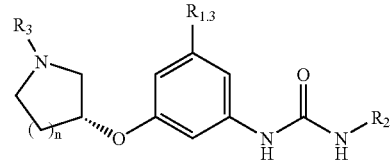

Formula I prepared by a method of claim 1, wherein
$R_{1.3}$ is chosen from hydrogen, halo, optionally substituted heteroaryl, and nitro;
$R_2$ is chosen from optionally substituted aryl, optionally substituted aralkyl, optionally substituted cycloalkyl, optionally substituted heteroaryl, optionally substituted heteroaralkyl, and optionally substituted heterocyclyl;
$R_3$ is chosen from optionally substituted acyl, optionally substituted alkoxycarbonyl, amidino, and sulfonyl; and
n is 1 or 2.

* * * * *